US010874397B2

(12) United States Patent
Beisel et al.

(10) Patent No.: US 10,874,397 B2
(45) Date of Patent: *Dec. 29, 2020

(54) MAGNETIC ANASTOMOSIS DEVICES WITH VARYING MAGNETIC FORCE AT A DISTANCE

(71) Applicant: G.I. Windows, Inc., West Bridgewater, MA (US)

(72) Inventors: Robert F. Beisel, Robesonia, PA (US); Marvin Ryou, Melrose, MA (US); Christopher Thompson, Needham, MA (US)

(73) Assignee: G.I. Windows, Inc., West Bridgewater, MA (US)

( * ) Notice: Subject to any disclaimer, the term of this patent is extended or adjusted under 35 U.S.C. 154(b) by 119 days.

This patent is subject to a terminal disclaimer.

(21) Appl. No.: 15/991,242

(22) Filed: May 29, 2018

(65) Prior Publication Data

US 2018/0271531 A1    Sep. 27, 2018

Related U.S. Application Data

(63) Continuation of application No. 15/068,441, filed on Mar. 11, 2016, now Pat. No. 10,517,600.

(Continued)

(51) Int. Cl.
*A61B 5/11* (2006.01)
*A61B 17/11* (2006.01)
(Continued)

(52) U.S. Cl.
CPC ..... *A61B 17/1114* (2013.01); *A61B 17/12163* (2013.01); *A61B 2017/00876* (2013.01);
(Continued)

(58) Field of Classification Search
CPC ...... A61B 34/30; A61B 17/1114; A61F 2/064
See application file for complete search history.

(56) References Cited

U.S. PATENT DOCUMENTS 10,517,600 B2 *  12/2019  Beisel ............... A61B 17/1114
2005/0283235 A1  12/2005  Kugler et al.
(Continued)

FOREIGN PATENT DOCUMENTS

| EP | 1894514 A2 | 3/2008 |
|---|---|---|
| WO | 01/087398 A2 | 11/2001 |
| WO | 2013/009886 A1 | 1/2013 |

OTHER PUBLICATIONS

Search Report and Written Opinion dated May 30, 2016 in counterpart international application PCT/US2016/022209.

*Primary Examiner* — Richard G Louis
(74) *Attorney, Agent, or Firm* — Nutter McClennan & Fish LLP

(57) ABSTRACT

Magnetic anastomosis devices constructed from magnetic segments coupled together with members that help the devices spontaneously transform from a linear delivery configuration to a polygonal deployment configuration. When two devices are joined together over tissue(s), the compressive force causes the tissue(s) to necrose and form an anastomosis. By altering the arrangement of the magnetic poles of the magnetic segments in the devices, the magnetic interaction between paired devices can be altered. This property gives surgeons flexibility in choosing how much attractive force the devices will experience during a procedure.

20 Claims, 33 Drawing Sheets

Related U.S. Application Data

(60) Provisional application No. 62/132,075, filed on Mar. 12, 2015.

(51) Int. Cl.
 *A61B 17/00* (2006.01)
 *A61B 17/12* (2006.01)

(52) U.S. Cl.
 CPC .................. *A61B 2017/1117* (2013.01); *A61B 2017/1139* (2013.01)

(56) References Cited

U.S. PATENT DOCUMENTS

| | | |
|---|---|---|
| 2009/0125042 A1 | 5/2009 | Mouw |
| 2013/0253550 A1 | 9/2013 | Beisel et al. |

\* cited by examiner

Configuration 1 (NNNN)

1 NonQ    8 Repel           +8
1 +2Q     6 Repel, 2 Attract   +4

(vii)

(i)

(iv)

(ii)

(vi)

(v)

(iii)

(viii)

Configuration 2 (NNNS)

(i)

| 2 NonQ | 6R + 2A | +8 |
|---|---|---|
| 2 +2Q | 4R + 4A | 0 |

(vii)

(iv)

(ii)

(vi)

(v)

(iii)

(viii)

Configuration 3 (NNSN)

| | | |
|---|---|---|
| 3 NonQ | 4R + 4A | 0 |
| 3 +2Q | 2R + 6A | -4 |

(vii)

(i)

(iv)

(ii)

(vi)

(v)

(iii)

(viii)

Configuration 6 (NNSS)

| | | |
|---|---|---|
| 6 NonQ | 6R + 2A | -4 |
| 6 +2Q | 4R + 4A | 0 |

(i)

(vii)

(iv)

(ii)

(vi)

(v)

(iii)

(viii)

Configuration 7 (NSSN)

| | | |
|---|---|---|
| 7 NonQ | 4R + 4A | 0 |
| 7 +2Q | 2R + 6A | -4 |

(vii)

(i)

(iv)

(ii)

(vi)

(v)

(iii)

(viii)

Configuration 10 (NSNS)

10 NonQ   6R + 2A   -4
10 +2Q    8A        -8

(vii)

(i)

(iv)

(ii)

(vi)

(v)

(iii)

(viii)

MAGNETIC ANASTOMOSIS DEVICES WITH VARYING MAGNETIC FORCE AT A DISTANCE

CROSS-REFERENCE TO RELATED APPLICATIONS

This application claims the benefit of, and priority to, U.S. application Ser. No. 15/068,441, filed Mar. 11, 2016, which claims the benefit of, and priority to, U.S. Provisional Application Ser. No. 62/132,075, filed Mar. 12, 2015, the contents of each of which are hereby incorporated by reference herein in their entirety.

FIELD OF THE INVENTION

The invention relates to deployable magnetic compression devices and their use for creating anastomoses, e.g., in the gastrointestinal tract. The devices are especially useful for minimally-invasive delivery, e.g., using endoscopic and/or laparoscopic techniques.

BACKGROUND

Bypasses of the gastroenterological (GI), cardiovascular, or urological systems are typically formed by cutting holes in tissues at two locations and joining the holes with sutures or staples. A bypass is typically placed to route fluids (e.g., blood, nutrients) between healthier portions of the system, while bypassing diseases or malfunctioning tissues. The procedure is typically invasive, and subjects a patient to risks such as bleeding, infection, pain, and adverse reaction to anesthesia. Additionally, a bypass created with sutures or staples can be complicated by post-operative leaks and adhesions. Leaks may result in infection or sepsis, while adhesions can result in complications such as bowel strangulation and obstruction. While traditional bypass procedures can be completed with an endoscope, laparoscope, or robot, it can be time consuming to join the holes cut into the tissues. Furthermore, such procedures require specialized expertise and equipment that is not available at many surgical facilities.

As an alternative to sutures or staples, surgeons can use mechanical couplings or magnets to create a compressive anastomosis between tissues. For example, compressive couplings or paired magnets can be delivered to tissues to be joined. Because of the strong compression, the tissue trapped between the couplings or magnets is cut off from its blood supply. Under these conditions, the tissue becomes necrotic and degenerates, and at the same time, new tissue grows around points of compression, e.g., on the edges of the coupling. With time, the coupling can be removed, leaving a healed anastomosis between the tissues.

Nonetheless, the difficulty of placing the magnets or couplings limits the locations that compressive anastomosis can be used. In most cases, the magnets or couplings have to be delivered as two separate assemblies, requiring either an open surgical field or a bulky delivery device. For example, existing magnetic compression devices are limited to structures small enough to be deployed with a delivery conduit e.g., an endoscopic instrument channel or laparoscopic port. When these smaller structures are used, the formed anastomosis is small and suffers from short-term patency.

An additional difficulty arises in that a surgeon typically cannot control the amount of magnetic attraction between deployable magnetic structures used to create an anastomosis. In some instances, it is beneficial for the magnetic devices to couple strongly at distances over 1 cm, however, in other instances, it is beneficial if the devices couple weakly at over 1 cm, and then lock together at a smaller distances. When the magnetic force is stronger than needed for a procedure, the devices may "jump" or spontaneously move together before the surgeon is ready for the devices to couple and may inadvertently trap tissues that are not intended to be joined.

Thus, there still remains a clinical need for reliable devices and minimally-invasive procedures that facilitate compression anastomosis formation between tissues in the human body.

SUMMARY

The invention provides improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer.

The invention provides multiple configurations of magnetic devices comprising an assembly of magnetic segments that can be used to create anastomoses in a subject. Some of the devices are self-opening, and designed to be delivered via a trocar using laparoscopic techniques. The self-opening devices are constructed from an assembly of magnetic segments including connection members between adjacent segments. Some of the connection members may serve as hinges so as to allow adjacent magnetic segments to move relative to one another, particularly when the device transitions between delivery and deployed configurations, while one or more of the connection members may serve as a spring or other device for directing the magnetic segments to open to form a polygon.

For example, in one embodiment, the device includes an assembly including a first pair of magnetic segments coupled together with a first connection member and a second pair of magnetic segments coupled together with a second connection member. The assembly includes a delivery configuration in which the magnetic segments are aligned in two rows, the two rows being joined by the first and second connection members or one or more additional connection members coupling the first and second pairs of magnetic segments to one another. The assembly further includes a deployed configuration in which the magnetic segments form an open polygon based, at least in part, on a force provided by at least one of the first and second connection members or the additional connection members. Accordingly, at least one of the first and second connection members includes a spring, so as to direct the magnetic segments to open upon deployment.

The devices of the invention include a variety of configurations constructed from magnetic segments. Each magnetic segment has a north and a south magnetic pole. A device of the invention may include, for example, four segments allowing the deployed device to take the shape of a square. Alternatively, the device may include eight segments, allowing the device to take the shape of an octagon. Other arrangements are also feasible, including hexagons, decagons, dodecagons, tetradecagons, hexadecagons, etc.

In the deployed configuration, the polygon has a top and a bottom, and the magnetic segments can be arranged such that all or some of the north poles of the magnetic segments are arranged toward the top of the polygon. The inventors have discovered that for a given number of magnetic segments in a pair of devices, e.g., eight segments, different arrangements of north and south poles will result in different magnetic fields at a distance for the paired devices. However, the different arrangements will experience approximately the same attractive magnetic force when the devices are in close proximity, i.e., touching. This feature can be used to achieve variable magnetic force between paired devices during a surgical procedure in which an anastomosis is to be created. For example, if a surgeon decides after visualizing the surgical field that he will need maximum force at a distance to bring the tissues together, the surgeon may select a pair of devices in which all of the north poles are arranged in the same direction. However, if the surgeon decides that he would like to have a greater flexibility when arranging the devices, without having the devices couple prematurely, the surgeon may select a pair of devices in which the arrangement of the north and south poles are alternating for each magnetic element.

Using the disclosed magnetic devices, it is possible to form anastomoses in patients in need of such treatment. In an embodiment, two devices have deployed configurations with identical sizes, shapes, and magnetic polar arrangement. However, each device will have a different delivery configuration, thus allowing each device to be delivered with a different technique, e.g., one laparoscopically and one endoscopically. In an embodiment, one of the devices may include hinges at first and second ends of the device and polygon-opening members that direct the magnetic segments to open into a polygon upon deployment. This device can be delivered, e.g., via a trocar in a side-by-side delivery configuration. The other device may be constructed from magnetic segments coupled together in a linear arrangement with polygon-closing members that direct the device to close and form a polygon upon deployment. This device can be delivered via the working channel of an endoscope in a linear configuration.

Because of the variation in magnetic force at a distance, and the differences in delivery configurations, it will be advantageous to provide a set of matched devices in a kit. The kit may include a plurality of devices having the same delivery/deployment configuration but having different magnetic polar arrangements, or the kit may include a plurality of devices with the same magnetic polar arrangement but different delivery/deployment configurations. Other combinations of delivery/deployment configuration and magnetic polar arrangement are also possible.

In one aspect, the invention provides a self-opening magnetic compression anastomosis device. The device includes an assembly of at least four magnetic segments coupled end-to-end to form a polygon having an out-of-plane axis, wherein each magnetic segment has a north magnetic pole and a south magnetic pole. The assembly includes a first pair of magnetic segments coupled together with a first connection member and a second pair of magnetic segments coupled together with a second connection member. The assembly includes a delivery configuration in which the magnetic segments are aligned in two rows, the two rows being joined by the first and second connection members or one or more additional connection members coupling the first and second pairs of magnetic segments to one another, and a deployed configuration in which the magnetic segments form an open polygon based, at least in part, on a force provided by at least one of the first and second connection members or the additional connection members.

In some embodiments, the first pair of magnetic segments have their north poles aligned relative to one another with respect to the out-of-plane axis and the second pair of magnetic segments have their north poles aligned relative to one another with respect to the out-of-plane axis. In some embodiments, the north poles of the first pair of magnetic segments are aligned with the north poles of the second pair of magnetic segments with respect to the out-of-plane axis. In other embodiments, north poles of the first pair magnetic segments are anti-aligned with the north poles of the second pair of magnetic segments with respect to the out-of-plane axis.

In some embodiments, the first pair of magnetic segments have their north poles anti-aligned relative to one another with respect to the out-of-plane axis and the second pair of magnetic segments have their north poles anti-aligned relative to one another with respect to the out-of-plane axis. Yet still, in some embodiments, the north magnetic poles of the magnetic segments alternate in orientation with respect to a top and a bottom of the polygon from segment to segment.

In some embodiments, the assembly includes four magnetic segments. The polygon has a top and a bottom, and two magnetic segments have their north magnetic poles arranged toward the top of the polygon and two other magnetic segments have their north magnetic poles arranged toward the bottom of the polygon. The north magnetic poles of the magnetic segments alternate in orientation with respect to the top and bottom of the polygon from segment to segment. The assembly includes a first magnetic segment, a second magnetic segment immediately adjacent to the first magnetic segment, a third magnetic segment immediately adjacent to the second magnetic segment, and a fourth magnetic segment immediately adjacent to the third and first magnetic segments. The north magnetic poles of the first and third magnetic segments are arranged toward the top of the polygon and the north magnetic poles of the second and fourth magnetic segments are arranged toward the bottom of the polygon.

In some embodiments, the assembly includes eight magnetic segments such that the assembly further includes a third pair of magnetic segments coupled together with a third connection member and a fourth pair of magnetic segments coupled together with a fourth connection member. When in the delivery configuration, the magnetic segments are aligned in two rows, the two rows being joined by the first and third connection members or one or more additional connection members coupling at least two of the first, second, third, and fourth pairs of magnetic segments to one another, and a deployed configuration in which the magnetic segments form an open polygon based, at least in part, on a force provided by at least one of the first, second, third, and fourth connection members or additional connection members.

When including at eight magnetic segments, the polygon has a top and a bottom, and four magnetic segments have their north magnetic poles arranged toward the top of the polygon and four other magnetic segments have their north magnetic poles arranged toward the bottom of the polygon. The north magnetic poles of the magnetic segments alternate in orientation with respect to the top and bottom of the polygon from segment to segment. The assembly includes a first magnetic segment, a second magnetic segment immediately adjacent to the first magnetic segment, a third magnetic segment immediately adjacent to the second magnetic segment, a fourth magnetic segment immediately adjacent to the third magnetic segment, a fifth magnetic segment immediately adjacent to the fourth magnetic segment, a sixth magnetic segment immediately adjacent to the fifth magnetic segment, a seventh magnetic segment immediately adjacent to the sixth magnetic segment, and an eighth magnetic segment immediately adjacent to the first and seventh magnetic segments. In embodiments, the north magnetic poles of the first, third, fifth, and seventh magnetic segments are arranged toward the top of the polygon and the north magnetic poles of the second, fourth, sixth, and eighth magnetic segments are arranged toward the bottom of the polygon.

Yet still, in embodiments in which the assembly includes eight magnetic segments, four adjacent magnetic segments have their north magnetic poles arranged toward the top of the polygon and four other adjacent magnetic segments have their north magnetic poles arranged toward the bottom of the polygon. The eight magnetic segments have their north magnetic poles aligned in the same direction with respect to the out-of-plane axis.

In some embodiments, one or more of the connection members includes a stainless steel, plastic, or nitinol material. In some embodiments, one or more of the connection members includes a spring. In some embodiments, one or more of the connection members includes a hinge. In some embodiments, one or more of the connection members is coupled to the exterior of the polygon. The one or more of the connection members may be an exoskeleton.

The polygon may include at least one of a square, hexagon, octagon, decagon, dodecagon, tetradecagon, hexadecagon, octodecagon, and icosagon.

When in the delivery configuration, the assembly of magnetic segments is sized to fit within a working channel of an access device and to be delivered to an anatomical structure within a patient. The assembly is configured to spontaneously convert from the delivery configuration to the deployed configuration once expelled from the working channel of the access device. The access device may include one of an endoscope, a laparoscope, a trocar, and a cannula.

In some embodiments, the assembly of magnetic segments is configured to be coupled to a guide element and configured to translate along a length of the guide element when transitioning from the delivery configuration to the deployed configuration. In some embodiments, the guide element may include a guidewire configured to fit within the working channel of the access device and coupled to the self-opening magnetic compression anastomosis device, wherein the assembly of magnetic segments is configured to translate along a length of the guidewire when transitioning from the delivery configuration to the deployed configuration.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

As shown in FIG. 3, the magnetic poles (N or S) of each magnetic segment can be arranged as desired. (For convenience, cross-hatching or shading corresponds to north magnetic pole);

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

The invention includes self-opening and self-closing polygonal magnetic devices that couple to each other with substantial compressive magnetic force. The invention makes it possible to create surgical anastomoses in tissue quickly with minimally-invasive techniques such as endoscopy and laparoscopy. Once the devices have are placed and mated, the compressive forces cause the vasculature of the tissue to collapse and fluids to extrude from the tissues, reducing the distance between the devices and increasing the magnetic attraction. With time, the coupled devices eventually mate completely, form an opening, and fall away from the tissue, leaving an anastomosis. The magnetic devices can, thus, be used to create surgical-quality anastomosis without the need to create an open surgical field.

With the described technique it is simpler to create openings between tissues that traditionally required open surgery or the use of complicated cutting and suturing devices. Most procedures are reduced to simply delivering a first magnetic compression device to a first tissue and then delivering a second magnetic compression device to a second tissue, and then bringing the two devices together. For example, it is straightforward to create a gastric bypass by delivering first and second magnetic devices, in the form of octagons, to the stomach and the small intestine. The magnetic force of the two devices eventually creates an anastomosis that leads from the stomach to the small intestine, reducing the working volume of the stomach.

The devices of the invention generally comprise magnetic segments that can assume a delivery conformation and a deployed configuration. The delivery configuration is typically linear so that the device can be delivered to a tissue via a laparoscopic "keyhole" incision or with delivery via a natural pathway, e.g., via the esophagus, with an endoscope or similar device. Additionally, the delivery conformation is typically somewhat flexible so that the device can be guided through various curves in the body. Once the device is delivered, the device will assume a deployed configuration of the desired shape and size by converting from the delivery configuration to the deployed configuration automatically. The self-conversion from the delivery configuration to the deployment configuration is directed by coupling structures that cause the magnetic segments to move in the desired way without intervention.

Figure 1:
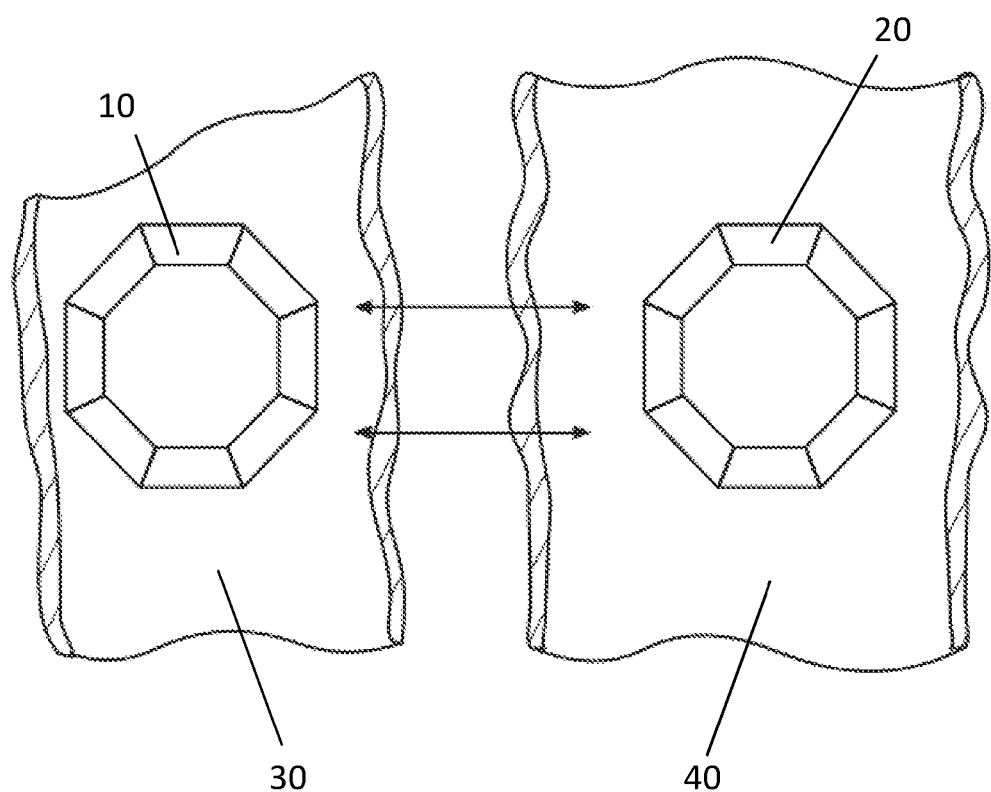
FIG. 1 depicts two magnetic devices attracting each other through tissue. The devices shown in FIG. 1 each comprise eight magnetic segments, however alternate configurations are possible. Once the two devices mate, the tissue that is trapped between the devices will necrose, causing an anastomosis to form. Alternatively, the tissue bound by the devices may be perforated after the devices mate to create an immediate anastomosis.

As shown in FIG. 1 two devices 10 and 20 are brought to opposite sides of tissues 30 and 40, in which an anastomosis is to be formed. Once the two devices 10 and 20 are brought into proximity, the devices 10 and 20 mate and bring the tissues 30 and 40 together. With time, an anastomosis of the size and shape of the devices 10 and 20 will form and the devices will fall away from the tissue. Alternatively, because the mated devices 10 and 20 create enough compressive force to stop the blood flow to the tissues 30 and 40 trapped between the devices, a surgeon may create an anastomosis, by making an incision in the tissues 30 and 40 circumscribed by the devices. In yet another embodiment, a surgeon may first cut into the tissue, e.g., tissue 30, and then deliver the device 10 around the incision and then couple the second device 20 to the first device so that the devices 10 and 20 circumscribes the incision. As before, once the devices mate, the blood flow to the incision is quickly cut off. The mating device 20 may be delivered in the same way, e.g., through an incision, or the mating device 20 can be delivered via a different surgical route, e.g., via an endoscope.

During the procedure, the position of the two devices 10 and 20 can be visualized directly, e.g., using an endoscopic or laparoscopic camera. In other instances, the two devices 10 and 20 can be monitored with ultrasound or another medical imaging technique, such as fluoroscopy. In some embodiments, the visualization will be provided with the delivery device. In some embodiments, the visualization will be achieved with a separate device. Other techniques, known in the art, such as dyes, contrast, and gas delivery may also be used to assist visualization of the mating devices.

As described in greater detail below, the design of the devices 10 and 20 can be customized depending upon the surgical techniques that will be used and the specific needs of the patient. The design specifications may include: required capture range, desired effective inner and outer diameters of the magnetic device (e.g., as defined by the desired anastomosis size and instrument passage), thickness of the target tissue, and the inner diameter of the guiding channel and the smallest radius of curvature to which the guiding channel may be bent and through which the magnets must pass. Once the design specifications are chosen, corresponding magnetic device designs can be determined, such as polygon-side-count and length, and the maximum lateral dimensions of the flexible linear magnetic structure that will be deployed through the delivery instrument. Additionally, as described below, the arrangements of the magnetic segments that make up the device may be altered to customize the amount of force between the devices 10 and 20 at a distance, e.g., at 1 cm or further apart.

Figure 2:
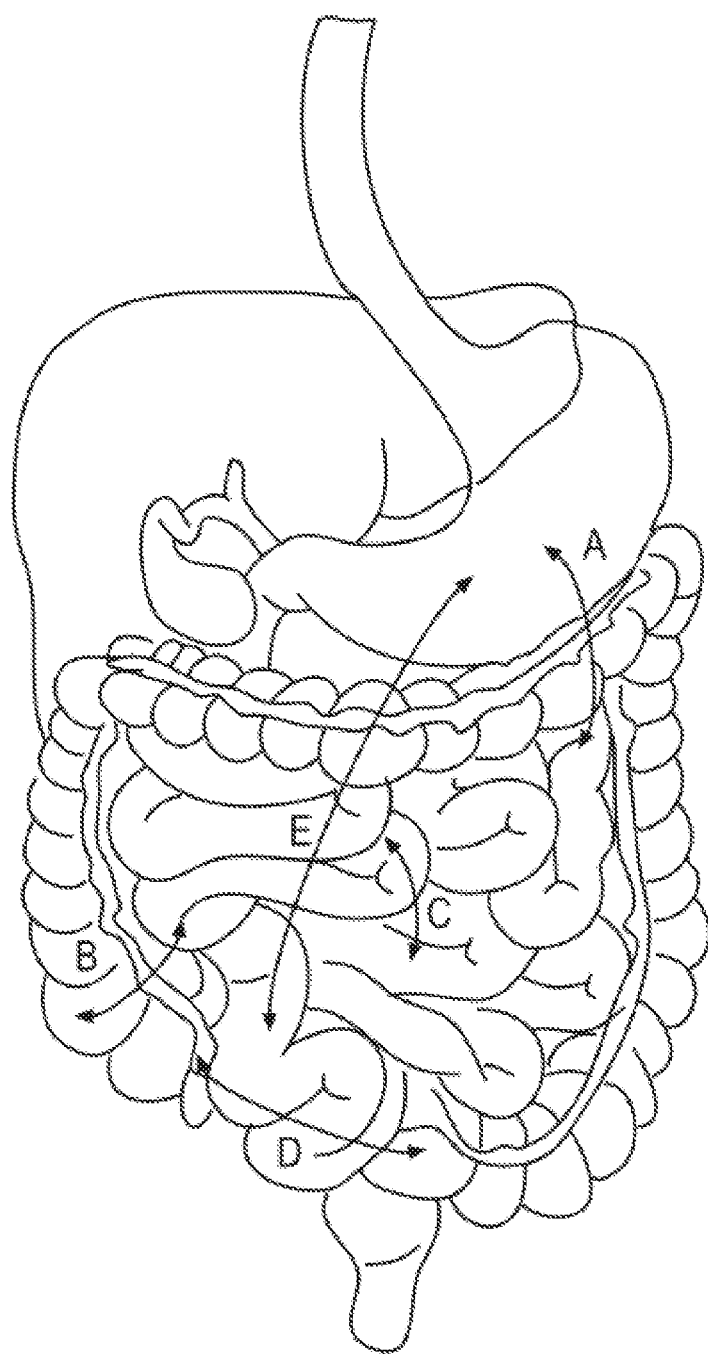
FIG. 2 depicts the creation of an anastomosis between organs of the gastrointestinal tract.

Using the techniques outlined above, it is possible to create anastomoses between a variety of tissues and organs in the gastrointestinal tract, as depicted in FIG. 2. For example, anastomoses may be formed between the stomach, small intestine, gall bladder, and colon, as shown in FIG. 2. Such techniques can be used for management of disease, such as obesity and diabetes, or such techniques can be used to improve function in the wake of disease, such as cancer. Such techniques can also be used for repair, for example, to connect portions of healthy colon after a portion of diseased colon has been removed. Such procedures can be accomplished endoscopically, laparoscopically, with an open surgical field, or with some combination of these techniques.

Figure 3:
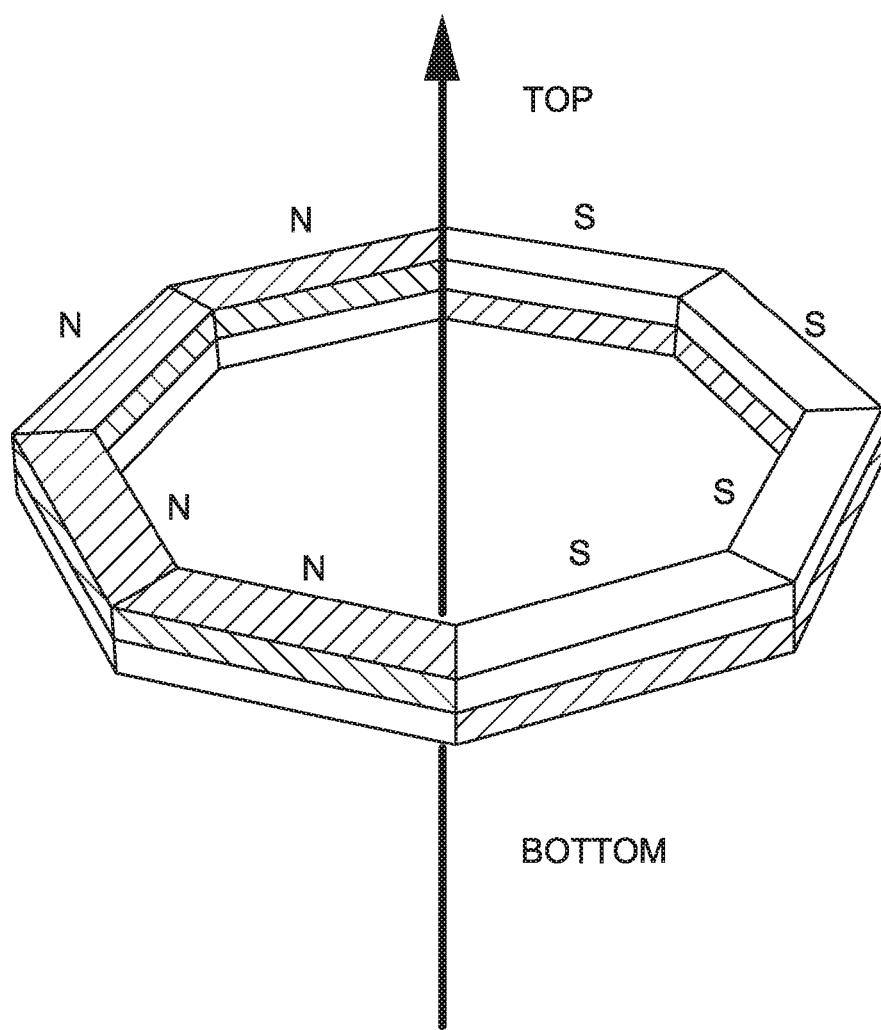
FIG. 3 depicts an octagonal device of the invention. The arrow depicts the out-of-plane axis for the device and defines a top and bottom.
Figure 4A:
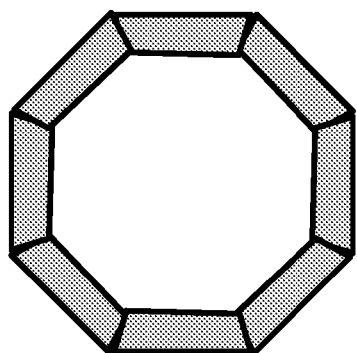
FIGS. 4A-4E depict exemplary configurations of devices comprising eight magnetic segments.
Figure 4B:
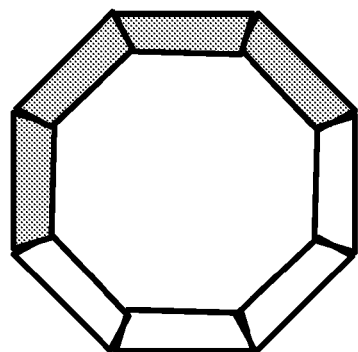
Figure 4C:
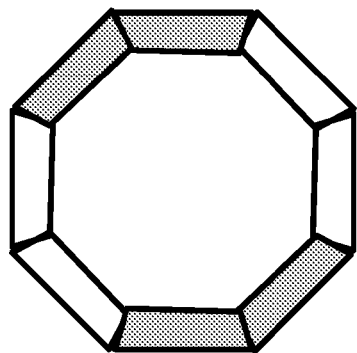
Figure 4D:
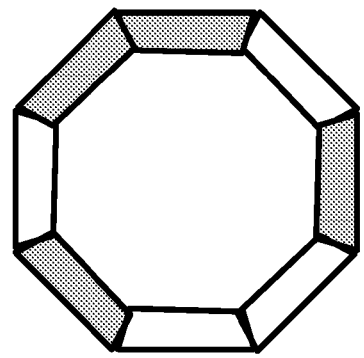
Figure 4E:
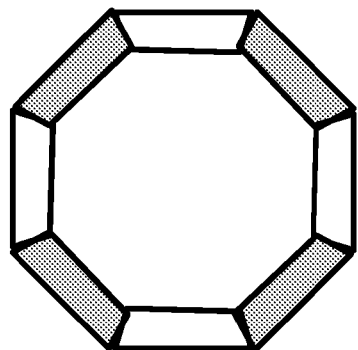
Figure 5A:
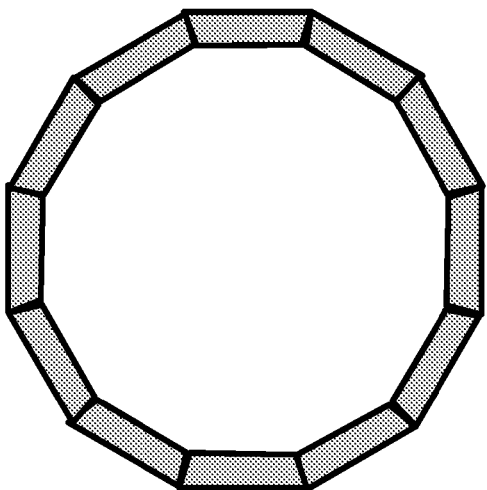
FIGS. 5A-5F depict exemplary configurations of devices comprising twelve magnetic segments.
Figure 5B:
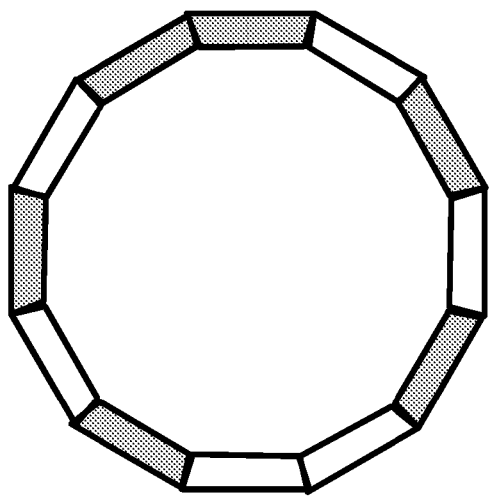
Figure 5C:
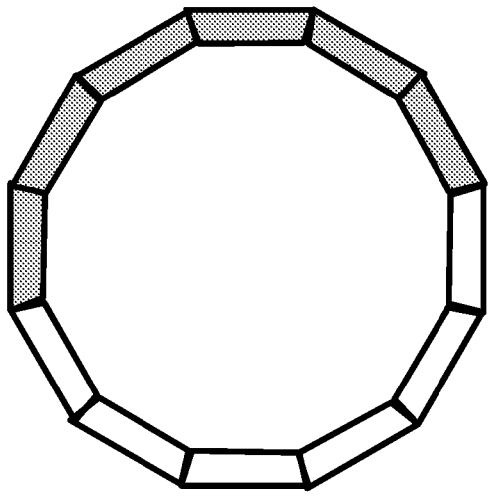
Figure 5D:
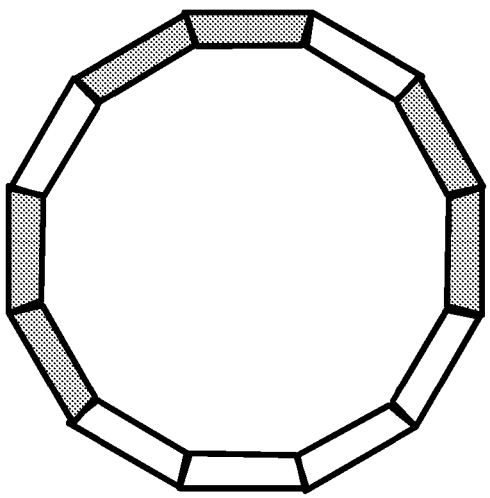
Figure 5E:
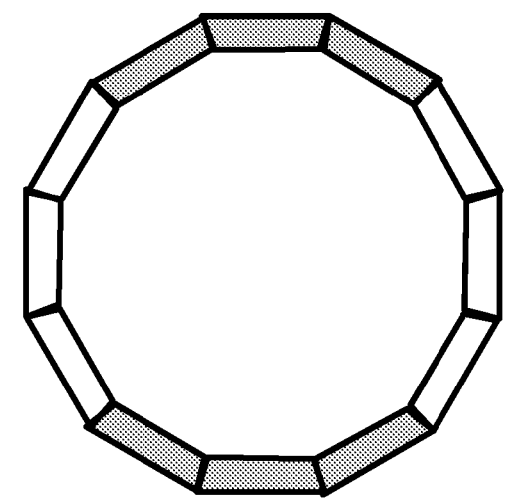
Figure 5F:
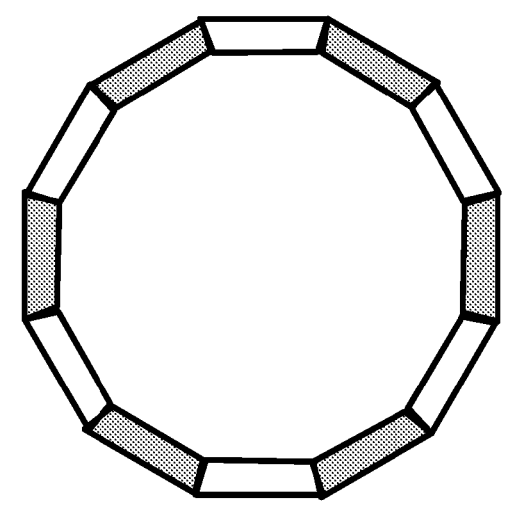

A device of the invention, generally, includes a plurality of magnetic segments that assume the shape of a polygon once deployed in a patient. The magnetic segments are typically formed from rare earth magnets. The magnetic segments may be mitered. The magnetic segments may be coated with gold or plastic to improve their performance. A general depiction of an octagonal device is shown in FIG. 3, however it is to be understood that a variety of deployed shapes are feasible using the same construction, such as squares, hexagons, decagons, dodecagons, tetradecagons, hexadecagons, octodecagons, and icosagons. As shown in FIG. 3, each magnetic segment of the device has at least at least two poles, north "N" and south "S," with the poles oriented normal to the face of the polygon. For convention, the north magnetic poles of the segments of the application are sometimes cross-hatched, while the south magnetic poles are solid (or not cross-hatched). As shown in FIG. 3, an out of plane axis can be defined that runs through the center of the polygon and normal to the face of the polygon, defining a "TOP" and a "BOTTOM" of the device. (It is understood that "TOP" and "BOTTOM" are arbitrary, but correspond to different sides of the polygon.)

Because each magnetic segment has at least one north pole and at least one south pole, it is possible to create devices of the invention with a variety of magnetic polar configurations. For example, the device shown in FIG. 3 includes four magnetic segments arranged toward the top of the polygon, and four magnetic segments arranged toward the bottom of the polygon. Furthermore, as show in FIG. 3, the four magnetic segments arranged toward the top of the polygon are all adjacent each other. Such a configuration may be written N/N/N/N/S/S/S/S or NNNNSSSS, or N4/S4. Other arrangements of the magnetic poles are possible in an octagonal device, such as shown in FIG. 4. For example, all of the poles can be arranged in the same direction, i.e., N/N/N/N/N/N/N/N or N8 (top left of FIG. 4), or the magnetic poles can be alternated in each segment, i.e., N/S/N/S/N/S/N/S or NSNSNSNS (bottom of FIG. 4). Other configurations of the magnetic poles are also available, such as N/S/N/SS/N/S/N or N2SNS2NS, or N/SS/NN/SS/N or N2S2N2S2, or NN/SSSS/NN or N2S4N2, all shown in FIG. 4.

The variety in magnetic polar configuration can be extended to other geometries with fewer or greater numbers of magnetic segments. For example, as shown in FIG. 5, a device with 12 segments can be arranged with N12, N6S6, N3S3N3S3, N2SNSNS2NSNS, N2SN2S4N2S, or NSNSNSNSNSNS. Of course, the mirror images are also possible, such as S2NS2N4S2N, however such configurations are actually identical when viewed from the other side. The same principles can be used for devices that have fewer segments, for example, four segments (N4, N2S2, and NSNS), or six segments (N6, N3S3, N2S2NS, and NSNSNS). The same principles can be used for devices that include more than twelve segments, for example, sixteen segments (N16, N8S8, N6SNS6NS, N4S4N4S4, N4S2N2S4N2S2, N4SNSNS4NSNS, N3SN3SNS3NS3, N2S2N2S2N2S2N2S2, N2S2NSNSN2S2N2S2, N2S2NSN2S2NSN2S2, and NSNSNSNSNSNSNSNS).

Figure 6:
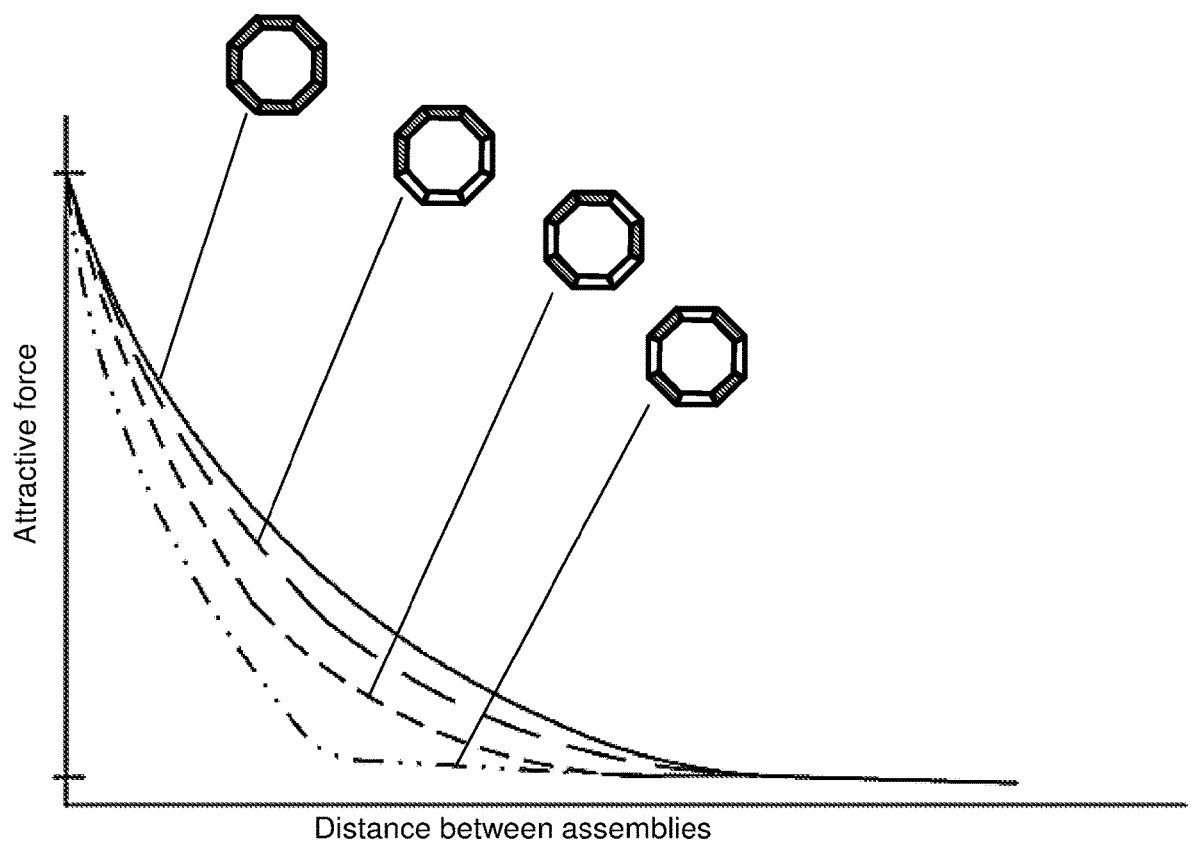
FIG. 6 shows a graphical depiction of the relationship between configuration of magnetic poles and attractive force at a distance for two paired devices having the same magnetic polar configuration.
Figure 7:
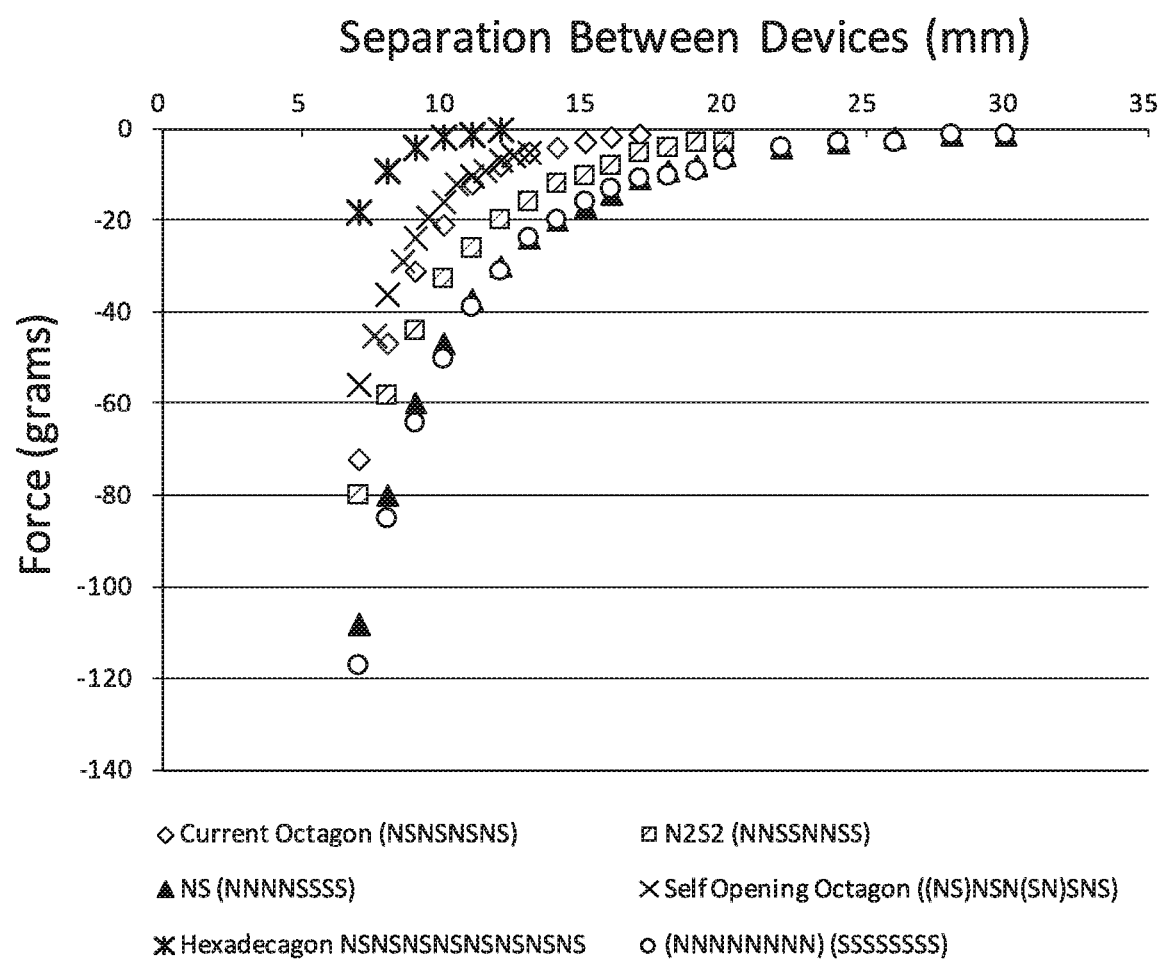
FIG. 7 shows a graphical depiction of the relationship between configuration of magnetic poles and attractive force at a distance for two paired devices having the same magnetic polar configuration.

The benefits of differing magnetic polar configurations are illustrated in FIG. 6. As depicted in the graph of FIG. 6, the relative attractive force between two octagons of identical magnetic polar configuration, as the devices are brought closer together, is a function of magnetic polar configuration. However, the total attractive force when devices of the same number of segments are brought into contact should be roughly the same. (The units on both axes are arbitrary, as is the variation between the curves.) In general, two devices having the magnetic poles of all of the magnetic segments arranged in the same direction with respect to top of the polygon experience the greatest amount of magnetic attraction at a distance (N8; solid line), while two devices having alternating magnetic poles in the magnetic segments have the least amount of magnetic attraction at a distance (NSNSNSNS; dot-dashed line). Intermediate to these two extremes are configurations in which the similarly-aligned magnetic segments are next to each other but not all poles are arranged in the same direction, i.e., N4S4 (long dashed line) and staggered configurations such as N2SNS2NS (short dashed line). Other configurations, not shown in the graph of FIG. 6, such as N7S, N5SNS, etc., would also have curves somewhere between the N8 curve and the NSNSNSNS curve. FIG. 7 shows actual force measurements made by securing magnetic arrangements in epoxy and bringing them toward each other with a dynamometer. As can be seen in FIG. 7, there is marginal difference in force at a distance between N8 and N4S4 octagons. It should be noted that, as shown in FIG. 7, there is a wide variation of force at a distance of approximately 1 cm (10 mm).

Figure 8:
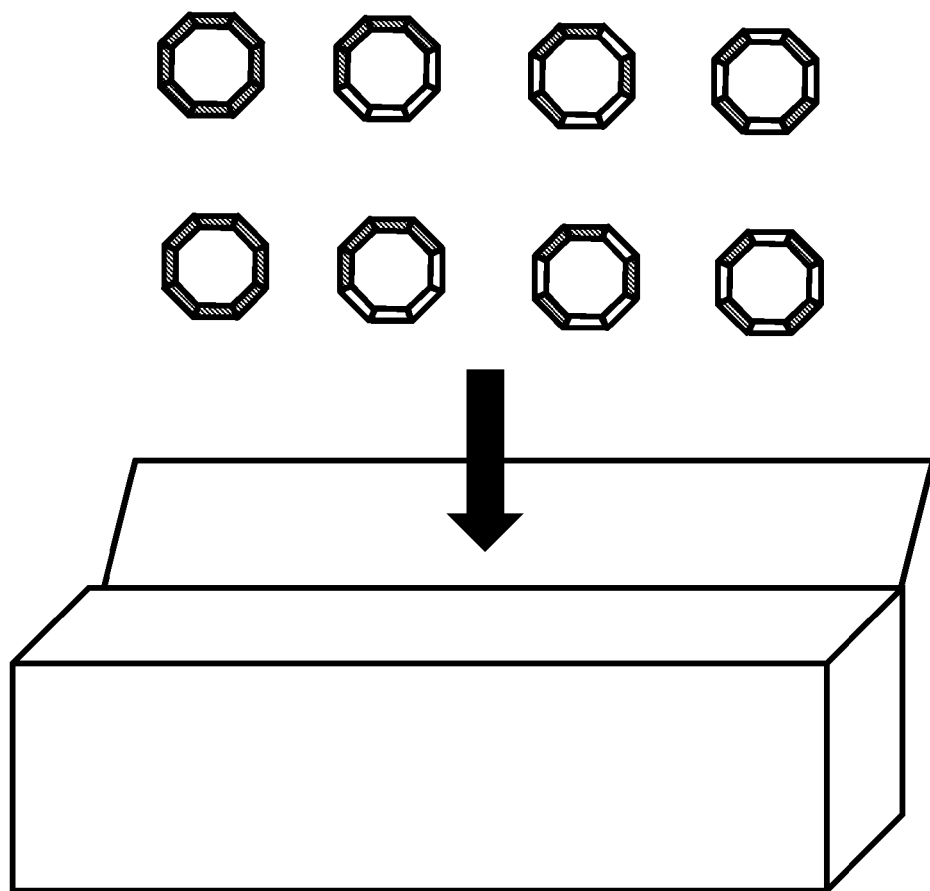
FIG. 8 depicts a kit containing a plurality of paired devices having differing magnetic polar arrangements. The paired devices may have the same or different delivery configurations.

Accordingly, by selecting a particular configuration, a surgeon can "tune" the interaction between devices for the desired performance. Thus, if it is necessary to maximize force at a distance to facilitate bringing tissues together, a surgeon can use two devices with all of the poles arranged in the same direction, i.e., N8. If, on the other hand, the placement of the devices was critical, and the surgeon wanted to minimize the chance that the devices mated before necessary, the surgeon could use a configuration with alternating magnetic poles, i.e., NSNSNSNS. In fact, for some procedures, it may be useful to provide a kit of matched devices with varying magnetic polar configurations, such as shown in FIG. 8. Such a kit would allow a surgeon to choose a desired configuration during the procedure, based upon visualization of the surgical field after the procedure has started. Alternatively, such a kit could provide "back-up," in the form of stronger-attracting devices, if the surgeon encountered difficulties joining the tissues during the procedure.

While not wishing to be limited by theory, it is believed that the variability between different magnetic polar configurations is a function of how much interaction a given magnetic pole has with segments of the same polarity on the mating device. That is, at intermediate distances, i.e., between no interaction and touching, each magnetic pole is interacting with multiple magnetic segments on the mating device. In the instance where mating devices comprise segments with alternating poles, a magnetic segment from a first device interacts with at least one opposite pole and two same poles on a nearby mating device. The same pole repulsions cancel out a good portion of the opposite pole attraction, resulting in less aggregate attraction at distances of about 1 cm or more. In the other extreme, a segment of a device having all of the poles arranged in the same direction would only experience attractive forces between it and the segments of the mating device.

Nonetheless, regardless of magnetic polar arrangements, once the two devices are brought together, most of the interaction is between a segment of the first device and the corresponding segment on the mating device. Accordingly, the total attractive force between devices of different configurations is about the same once the devices are joined.

In a similar fashion, devices of differing numbers of segments, i.e., squares, hexagons, octagons, decagons, dodecagons, tetradecagons, hexadecagons, octodecagons, and icosagons can be tuned by selecting particular arrangements of magnetic poles. There are also additional reasons that a particular configuration of magnetic poles may be chosen, for example, to cause the devices to overlap correctly, or to cause the devices to connect in a way that insures that the devices cannot revert to their delivery configuration. See e.g., US 2013/0253550, incorporated herein by reference in its entirety.

The variability in magnetic polar orientation, described above, can be used in a variety of deployable magnetic devices, including both self-opening and self-closing devices, as described below. For example, self-opening devices may be constructed having a variety of magnetic polar arrangements, as shown in FIGS. 9A-10B. Additionally, self-closing devices may be constructed having a variety of magnetic polar arrangements, as shown in FIGS. 12-15. As shown in FIGS. 11 and 16, the two configurations (self-opening and self-closing) lend themselves to deployment with different methods, i.e., laparoscopy and endoscopy, respectively. Accordingly, various combinations of devices can be selected, as required, based upon the surgical approach, and the requirements of the anatomy of the patient.

In some embodiments of the invention, the deployable magnetic device is self-opening, i.e., as shown in FIGS. 9A-10B. Each device comprises a number of magnetic segments 810, wherein two pairs of magnetic segments are linked together at each end with a connection member 830, such as a hinge. The magnetic segments 810 between the connection members 830 are linked together with additional connection members 850, which are configured to direct the device to self-convert from a delivery 870 to a deployed 890 configuration. It should be noted that the term "connection member" may be used herein to refer to a hinge or a polygon-opening member, depending on the application. For example, connection member 830 may be referred to herein as a "hinge", which connection member 850 may be referred to herein as a "polygon-opening member".

While the polygon-opening members 850 are shown coupled to the exterior of the magnetic segments in FIGS. 9A-10B, the polygon-opening members may also be coupled to the interior of the magnetic segments. In some instances, the polygon-opening members form an exoskeleton over the magnetic segments. The polygon-opening members may be bonded or fastened to the magnetic segments or the polygon-opening members can crimp or grab the magnetic segments.

While each self-opening device comprises two hinges, the number of polygon-opening members 850 depends upon the total number of magnetic segments in the device. For example, for a device that takes the configuration of a square upon deployment, the device will comprise four magnetic segments 810, two hinges 830, and two polygon-opening members 850. As shown in FIGS. 9A-10B, an octagonal self-opening device may include eight magnetic segments 810, two hinges 830, and six polygon-opening members 850. In alternate embodiments, a singular polygon opening member may span two or more magnetic segments 810 (shown in FIG. 10B). In alternative embodiments, as shown in FIG. 9B, a quadrupolar magnetic segment can be used at the hinge end to improve opening. Quadrupolar segments are not limited to octagonal configurations, and can be used with any of the configurations described herein. Thus, it is possible to construct a self-opening octagonal device with eight magnetic segments 810, two hinges 830, and two polygon-opening members (see FIG. 10B). Using the same techniques it is possible to construct deployable self-opening devices having different numbers of magnetic segments that deploy as, e.g., squares, hexagons, decagons, dodecagons, tetradecagons, hexadecagons, octodecagons, or icosagons.

The self-opening devices of the invention can incorporate a variety of magnetic polar configurations, as shown in FIGS. 9A-10B. However, because of the devices need to self-convert between a side-by-side arrangement and an open polygon, it is beneficial to place the hinges such that similarly-aligned magnetic poles are next to each other in the delivery configuration. For example, as shown in FIG. 10A, each segment in the delivery configuration is next to a segment of the same magnetic orientation so that, upon delivery, the magnetic repulsions between segments drives the device into the open (deployed) configuration. In such a configuration, the primary role of the polygon-opening member is to insure that the device opens in the plane of the polygon; i.e., that out-of-plane motion of the magnetic segments is limited. The hinges of the self-opening devices may be constructed from metal (stainless steel, nickel, or nitinol) or plastic, and the hinges may be passive or active, i.e., configured to provide an opening force. In some instances, the hinges are springs. The polygon-opening members may be constructed from constructed from metal (stainless steel, nickel, or nitinol) or plastic. The polygon opening members are typically active in that they provide a force to drive the device from a delivery configuration to a deployment configuration.

Figure 10A:
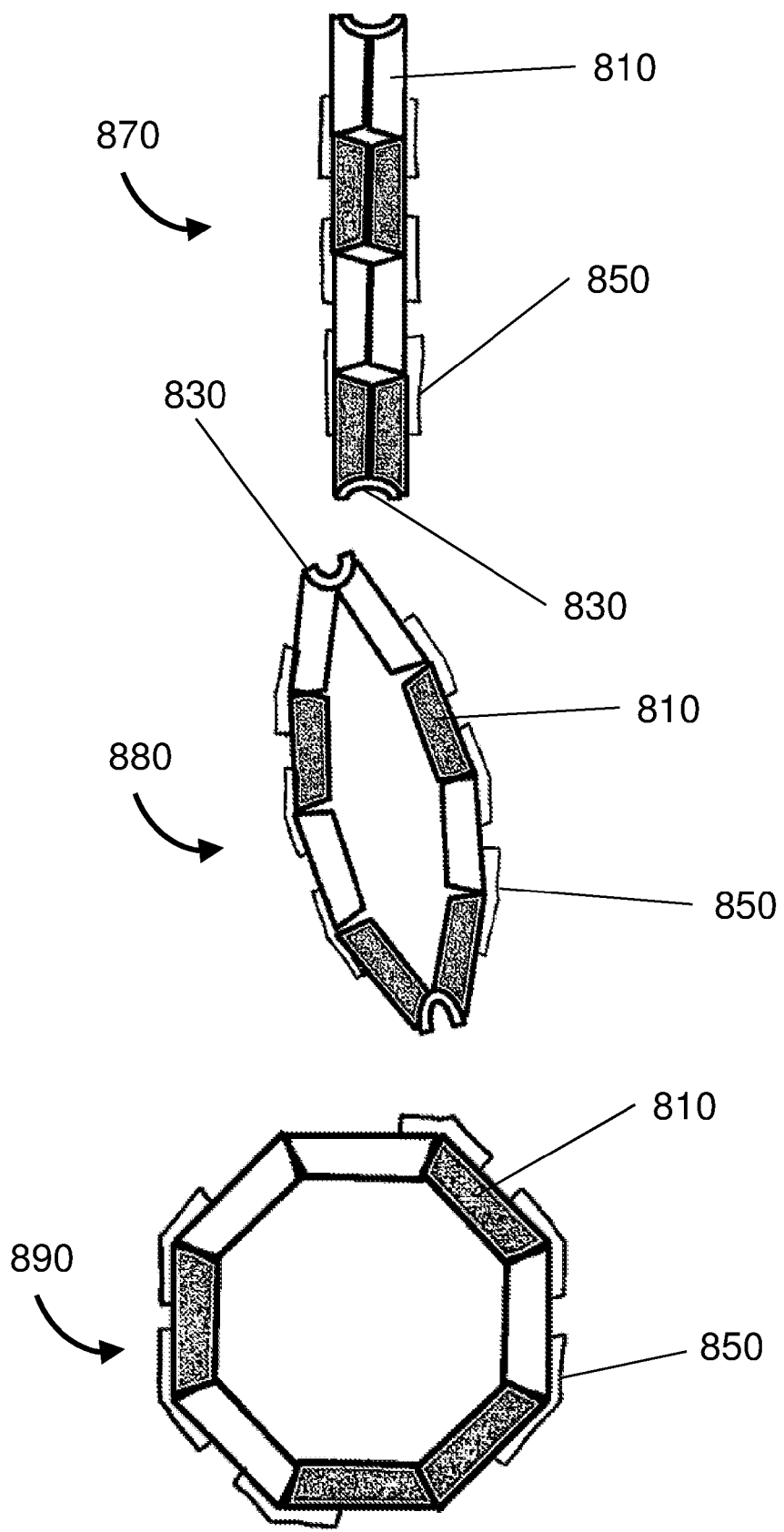
FIG. 10A is a close-up view of a self-opening magnetic anastomosis device of the invention including connection members at the ends and polygon-opening members between adjacent magnetic segments. In the embodiment of FIG. 10A, the poles of the magnetic segments alternate in direction around the polygon.
Figure 10B:
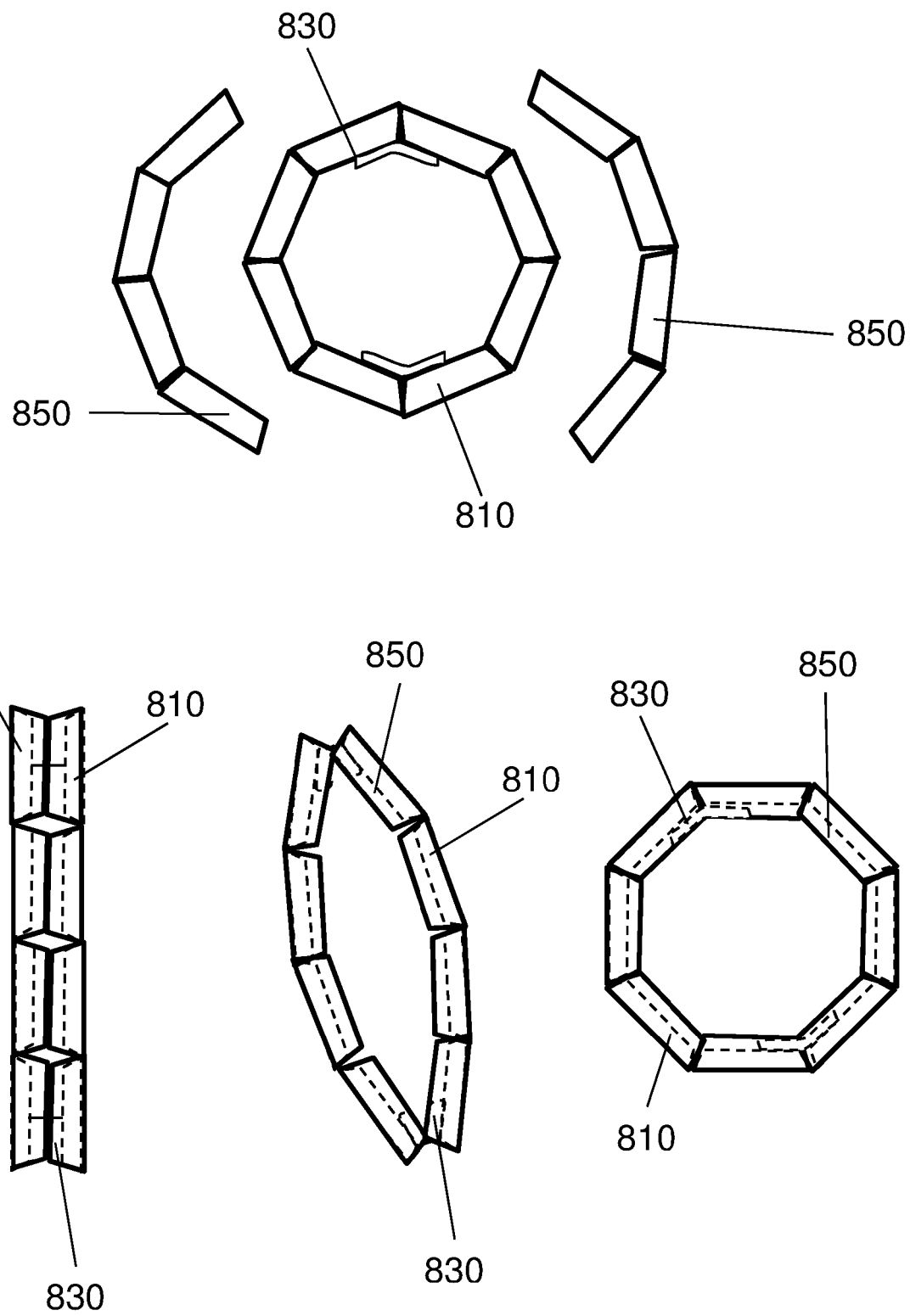
FIG. 10B is a close-up view of a self-opening magnetic anastomosis device of the invention including connection members at the ends and two polygon-opening members that span multiple adjacent magnetic segments. The polarities of the magnetic segments of FIG. 10B can be in any configuration, e.g., as shown in FIGS. 9A-10A.
Figure 11:
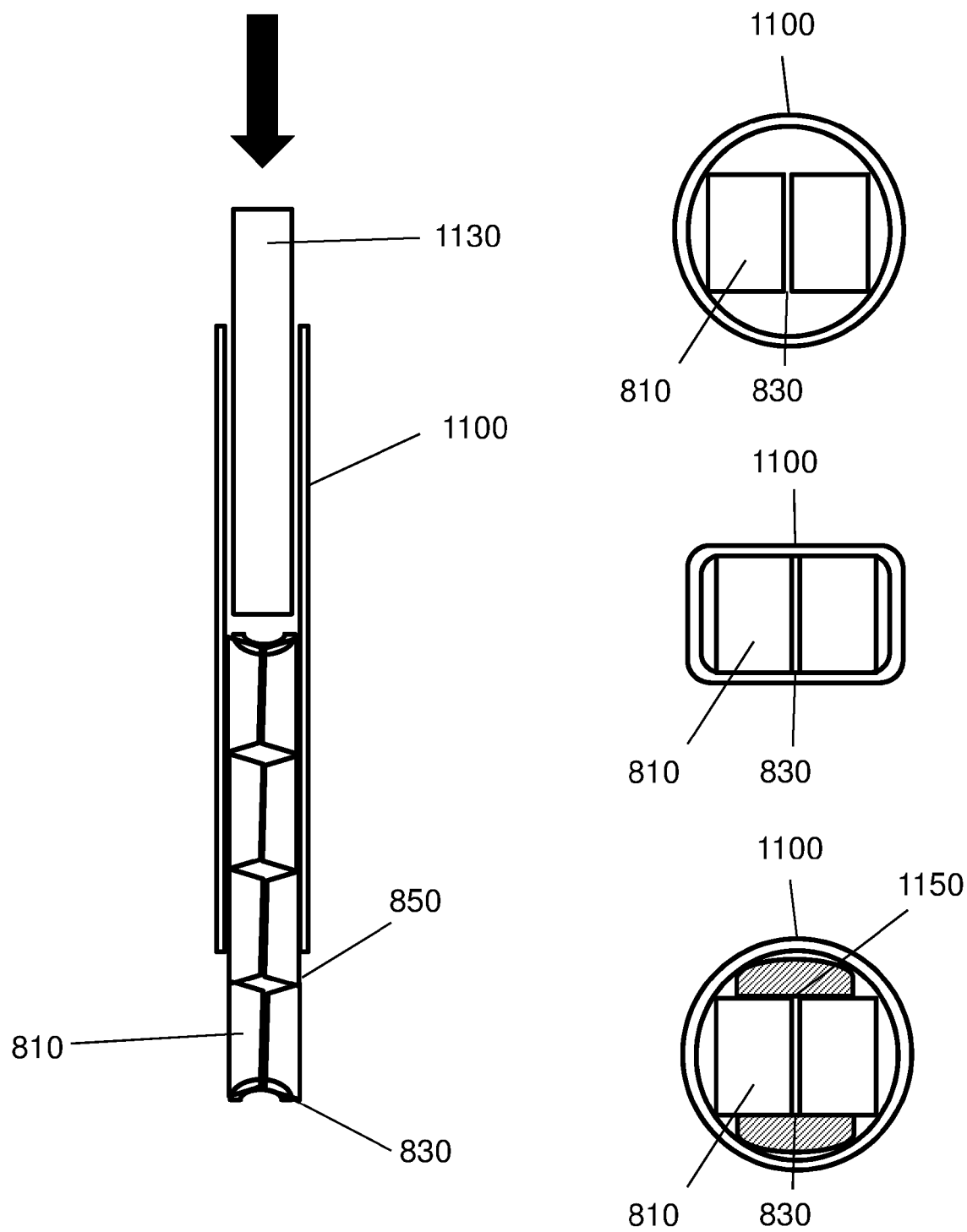
FIG. 11 depicts delivery of a self-opening magnetic anastomosis device of, e.g., FIGS. 9A-10A, through a trocar with the assistance of a pusher. In some embodiments, specialty trocars, such as a trocar having a rectangular cross-section or a round trocar having inserts, may be used to facilitate deployment of a self-opening device.

An alternate construction of an eight segment, self-opening device of the invention is shown in FIG. 10B. In the embodiment of FIG. 10B, only two polygon-opening members 850 are needed to direct the device to open properly. Like other self-opening devices, the device includes two hinges 830 that help the device transform from a delivery configuration (bottom left) to a deployed configuration (bottom right). The device shown in FIG. 10B may be constructed by first coupling two pairs of magnetic segments 810 with hinges 830, and then arranging the remaining magnetic segments 810 in a deployed configuration. Each polygon opening member 850 can then be coupled to four segments, including one segment of each hinged pair, to complete the assembly (top of FIG. 10B). The polygon opening members 850 may be bound, coupled, or attached to the magnetic segments. Alternatively, as shown in FIG. 10B, the polygon opening members 850 may envelop the magnetic segments, e.g., as an exoskeleton. While it is not shown in FIG. 10B, it is understood that the polarities of the magnetic segments 810 can be configured as desired to achieve specific performance at a distance, i.e., as discussed above with respect to FIGS. 3-6. Additionally, the construction shown in FIG. 10B is not limited to eight magnetic segments, as a polygon-opening member 850 can be coupled to many magnetic segments, such as two, three, four, five, six, seven, eight, nine, ten, eleven, twelve, thirteen, fourteen, or fifteen magnetic segments.

The self-opening devices of the invention are designed to be delivered in a side-by-side configuration as shown in FIG. 11. In this configuration, a self-opening device can be inserted through a trocar 1100 or other cannula to a location within a patient where the device will be deployed and coupled to a mating device. Typically, a pusher 1130 will be used to extract the self-opening device from the trocar 1100. Once the device is pushed from the trocar 1100, the device will spontaneously open to form a polygon, as shown in FIGS. 9A-10A. The trocar 1100 may be round in cross-section, or the trocar 1100 may be rectangular in cross-section to help the self-opening device to remain in a flat delivery configuration while it is delivered. (See right side of FIG. 11.) In other embodiments, non-magnetic inserts 1150, or extruded shaped tubing, may be used to facilitate delivery of a self-opening device. Other configurations of self-opening devices, i.e., squares, hexagons, decagons, dodecagons, tetradecagons, hexadecagons, octodecagons, and icosagons, can also be delivered in a similar manner. In some instances, the pusher may have a lumen for a guide element as discussed below. In some instances, a laparoscopic manipulator (not shown) will be used to facilitate placement of the deployed device.

Because of the construction, the magnetic devices of the invention are relatively smooth and flat and present essentially uninterrupted annular faces. Because of this design, the devices do not cut or perforate tissue(s), but rather achieve anastomosis by providing steady necrotizing pressure across the contact surface between mating deployed devices. These features also reduce the risks associated with surgical access and ensure that the anastomosis is formed with the correct geometric attributes. Overall, the design ensures the patency of the anastomosis.

Figure 12:
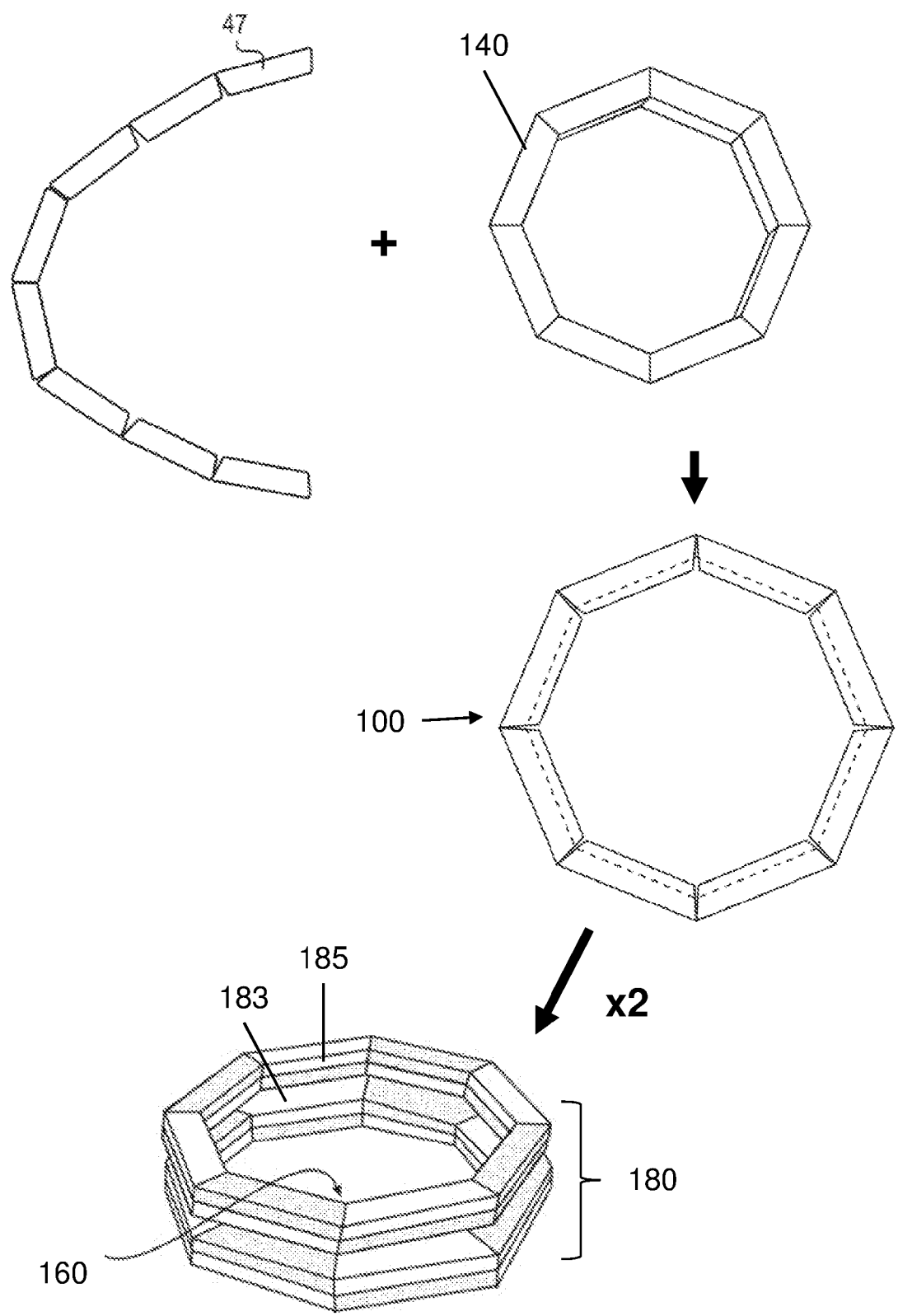
FIG. 12 depicts assembly of a self-closing magnetic anastomosis device that comprises a polygon-closing assembly (nitinol exoskeleton) and magnetic segments. Once assembled, two of the self-closing devices can be coupled together to form an anastomosis. The device of FIG. 12 has the magnetic poles of all eight magnets arranged in the same direction.

Like the self-opening devices of FIGS. 9A-10B, the self-closing devices of the invention can incorporate a variety of magnetic polar configurations, as shown in FIGS. 12-15. As shown in FIG. 12, a self-closing magnetic compression device 100 can be formed by delivering a polygon-closing assembly 120 to a set of magnetic segments 140. The polygon-closing assembly 120 may be made from a resilient material that will retain its shape after deformation, such as a polymer or metal alloy. In some embodiments, the metal alloy will comprise nickel, such as nitinol. The magnetic segments 140 may be comprised of any strongly-magnetic material, such as rare earth magnetics, comprising materials such as neodymium, samarium, erbium, yttrium, ytterbium, and cobalt. In some embodiments, the magnetic segments may be coated, e.g., with gold or Teflon, to improve durability or biocompatibility. Once assembled, the resulting self-assembling magnetic anastomosis device can be intentionally deformed into a semi-linear shape, but will form a polygon when released, as shown in FIG. 12.

During deployment, the polygon-closing assembly 120 acts as a hinge between magnetic segments 140 while coupling the structural rigidity of individual segments 140 similar to a cantilevered beam. In other words, the tensile modulus of the polygon-closing assembly 120 and the polygon-closing assembly's resistance to out-of-plane bending allow the forces on the distal end of the structure to be distributed across the magnetic segments 140. The design allows a pushing force on the proximal end of the device in a delivery configuration to reliably move the distal end of the device, e.g., out of a deployment lumen such as the working channel of an endoscope. Because the polygon-closing assembly 120 is thin, and in close contact with the magnetic segments that are long relative to the length of their miter joints, the polygon-closing assembly 120 can bend to accommodate miter closure with relatively small strain. However, the breadth of the polygon-closing assembly 120 produces a high moment of inertia (stiffness) against out-of-polygonal-plane bending, thereby giving good guidance of the growing ring and providing lateral resistance to deflection during closure. Finally, the polygon-closing assembly 120 also provides a tensile coupling between the magnetic segments, assuring that the segments do not go past the closure point and collapse inward or over top of one-another.

As show in FIG. 12, two self-assembling magnetic compression devices 100 can be associated as a matched set 180. As described above, tissues that are trapped between the matched set 180 will be compressed, and eventually grow together, leaving an opening 160 in the tissue. As shown in FIG. 12, each magnetic segment of the matched set 180, has at least at least two poles 183 and 185, with the poles oriented normal to the face of the polygon. When assembled, the poles of the segments in adjoining devices are arranged N/S/N/S or S/N/S/N. The aligned and matching poles in the matched set 180 form a very strong coupling between the two elements. Additionally, the attractive forces between opposing poles of nearby magnetic segments facilitates assembly of matched set 180. Typically, the two elements of the matched set 180 need only to be placed in proximity to each other and the magnetic segments will self-align in the preferred configuration. In some instances, it is necessary to pre-align the complimentary devices, however, in other instances the devices self-align by undergoing fast in-plane rotation with respect to one another.

Figure 13:
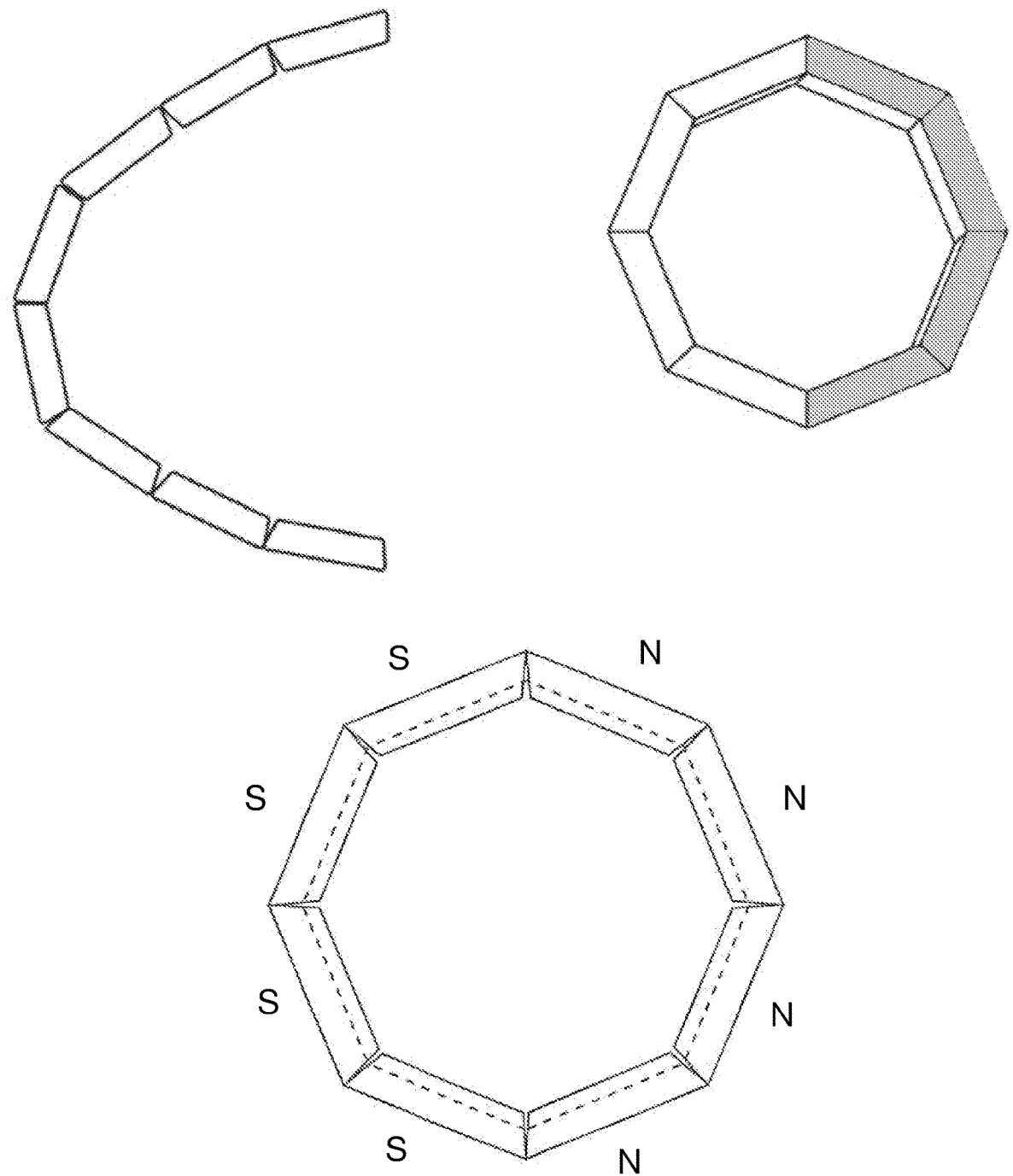
FIG. 13 depicts assembly of a self-closing magnetic anastomosis device that comprises a polygon-closing assembly (nitinol exoskeleton) and magnetic segments. The device of FIG. 13 has half of the poles of the magnetic segments arranged toward the top of the polygon and half of the poles of the magnetic segments arranged toward the bottom of the polygon.
Figure 14:
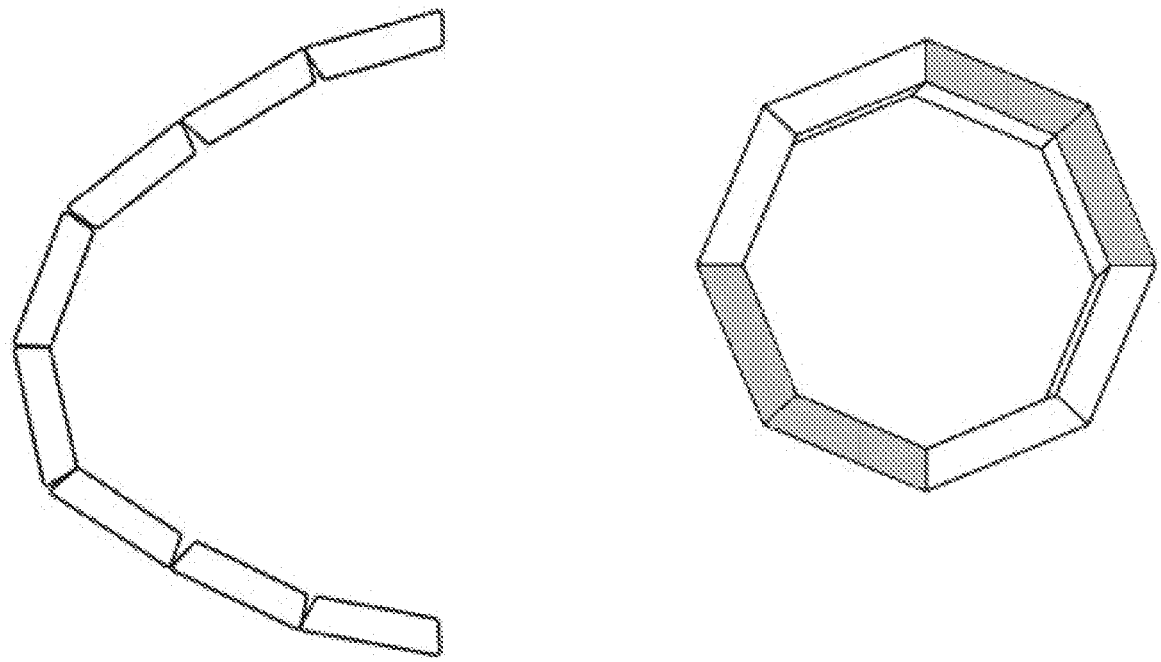
FIG. 14 depicts assembly of a self-closing magnetic anastomosis device that comprises a polygon-closing assembly (nitinol exoskeleton) and magnetic segments. The device of FIG. 14 has half of the poles of the magnetic segments arranged toward the top of the polygon and half of the poles of the magnetic segments arranged toward the bottom of the polygon.
Figure 14:
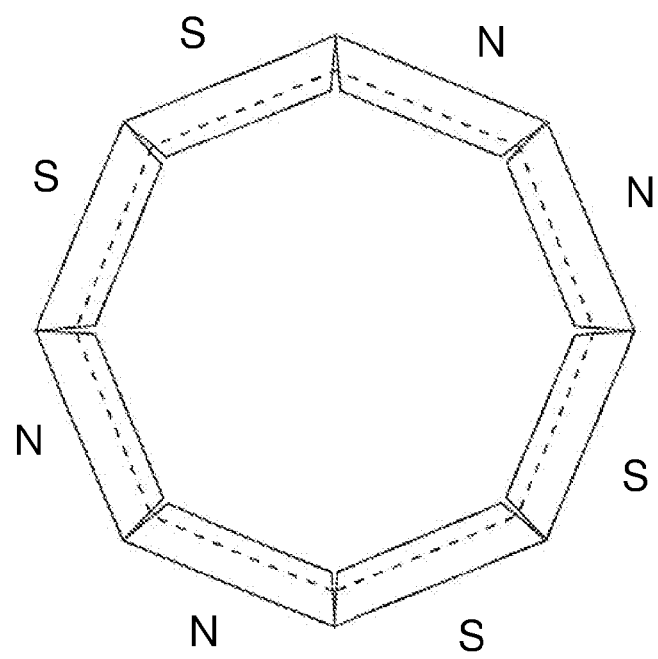
Figure 15:
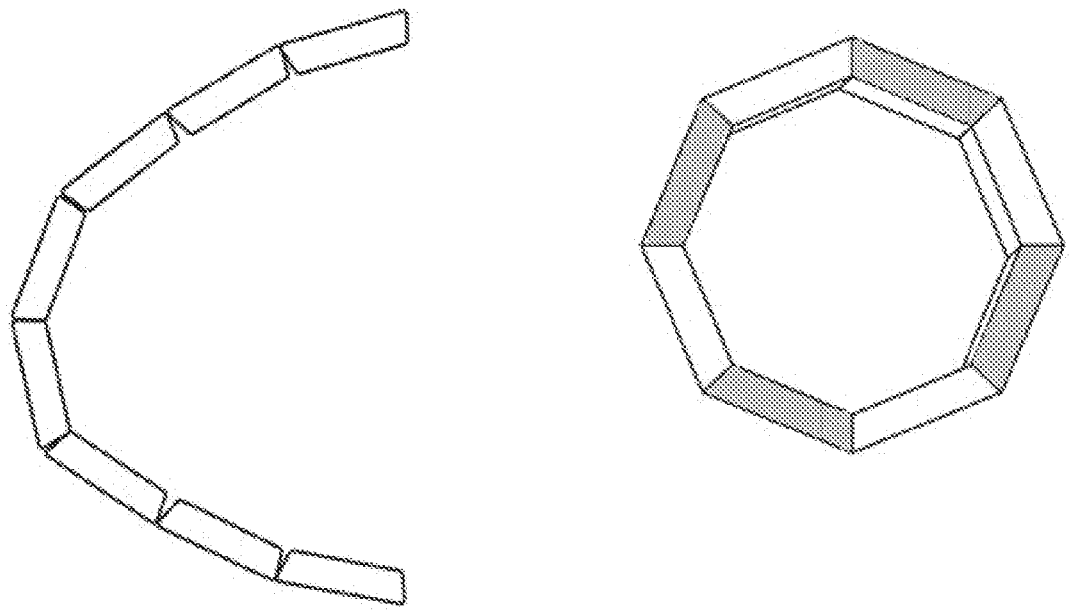
FIG. 15 depicts assembly of a self-closing magnetic anastomosis device that comprises a polygon-closing assembly (nitinol exoskeleton) and magnetic segments. In the embodiment of FIG. 15, the poles of the magnetic segments alternate in direction around the polygon.
Figure 15:
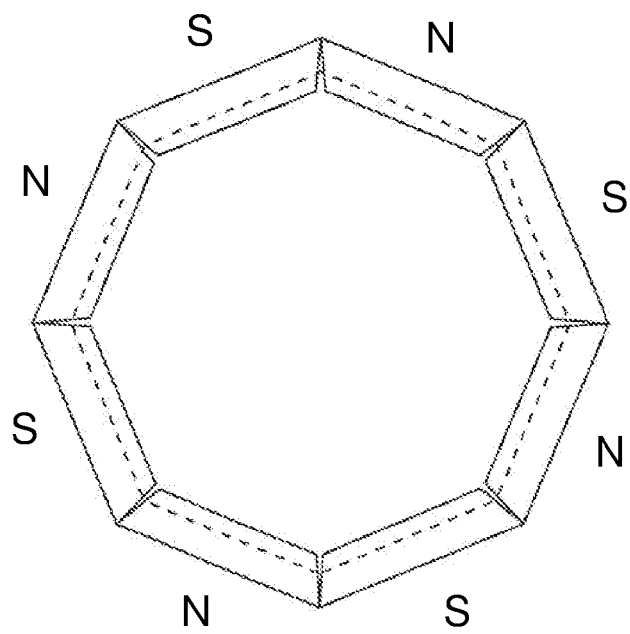
Figure 16:
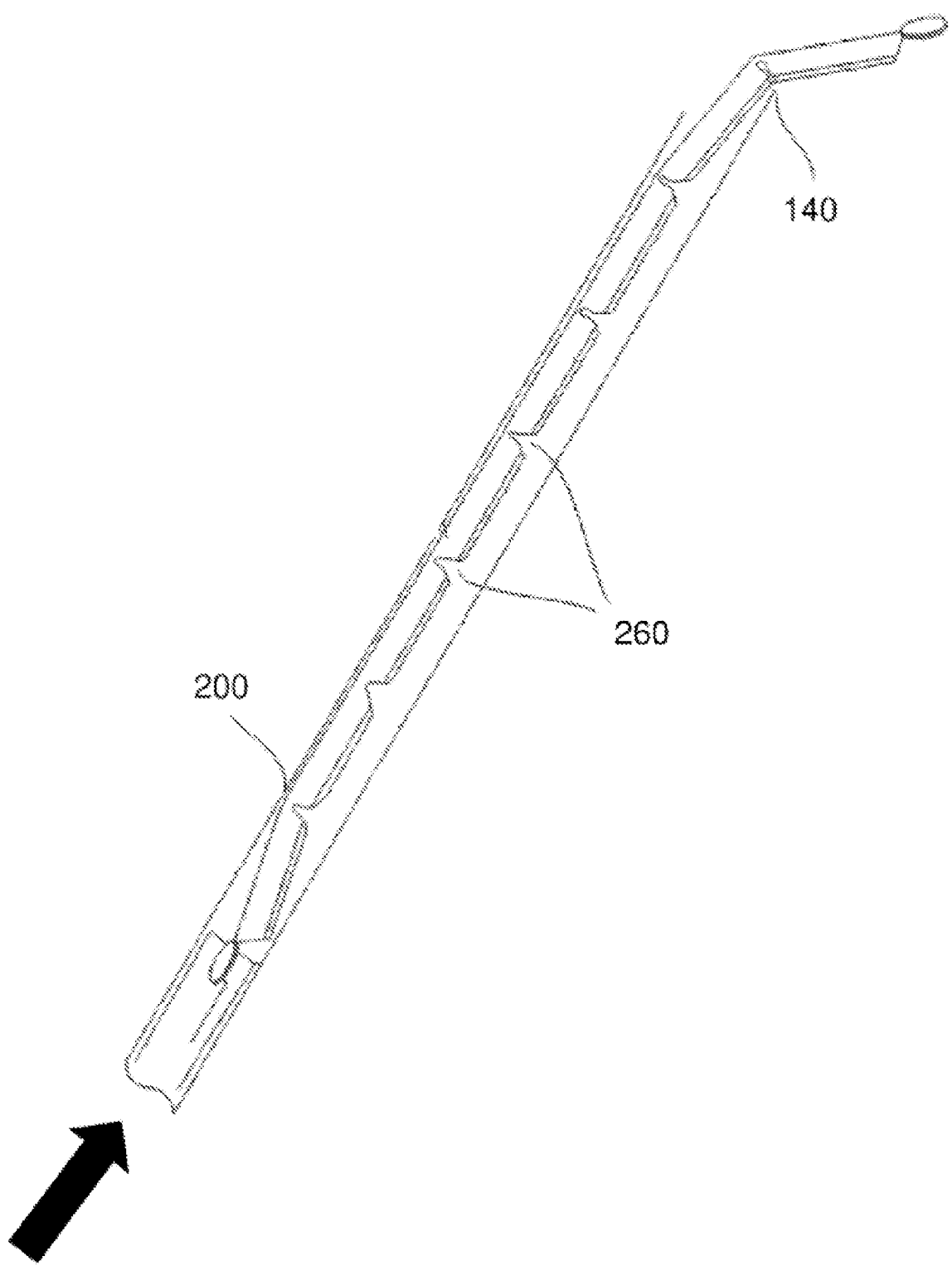
FIG. 16 depicts delivery of a self-closing magnetic anastomosis device of, e.g., FIGS. 12-15, through the working channel of an endoscope with the assistance of a pusher.
Figure 17:
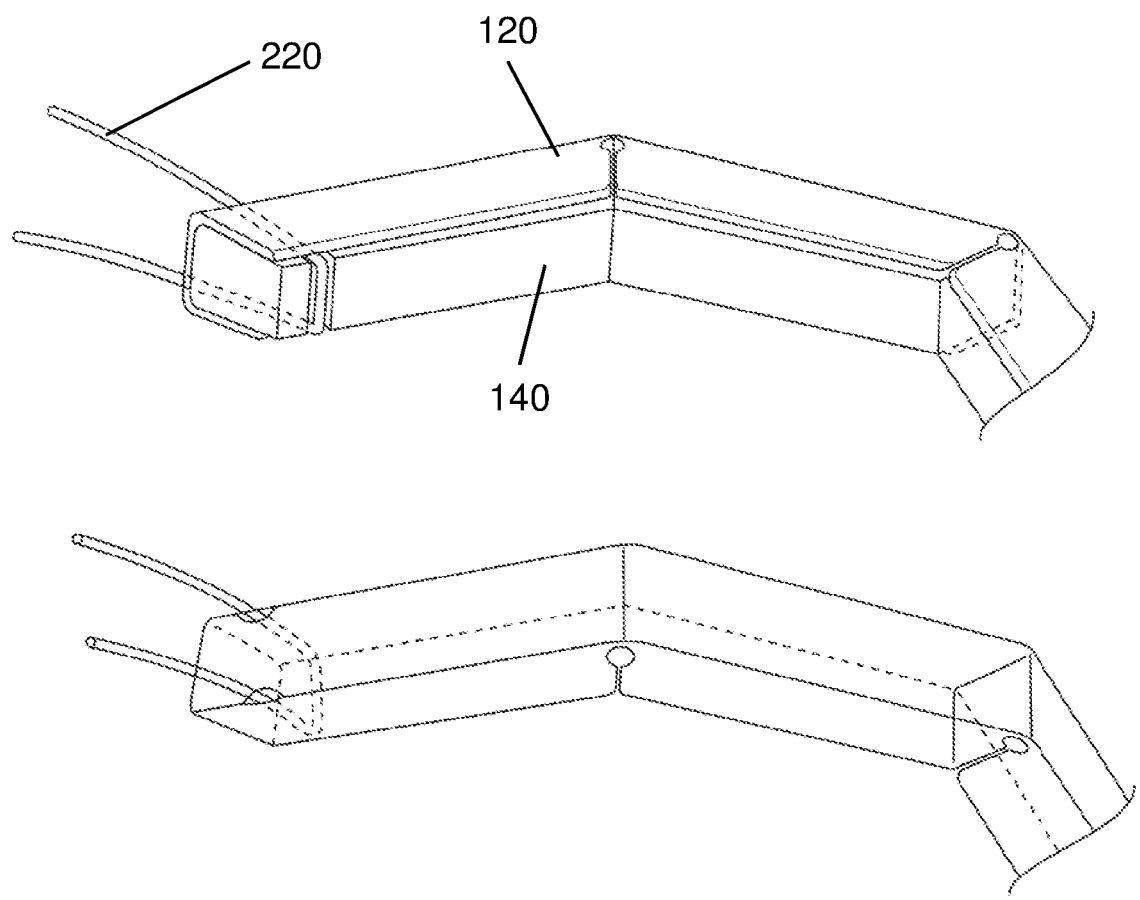
FIG. 17 shows an embodiment of a guide element coupled to a magnetic segment of a device of the invention. Alternate methods of coupling the guide element to the magnetic segment are also described herein.
Figure 18A:
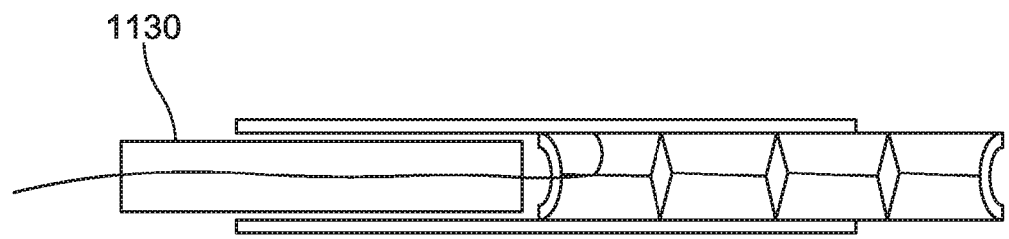
FIGS. 18A-18D depict an embodiment of a self-opening magnetic anastomosis device that includes a guide element coupled to an magnetic segment, wherein the guide element facilitates placement of the magnetic device in a deployment configuration.
Figure 18B:
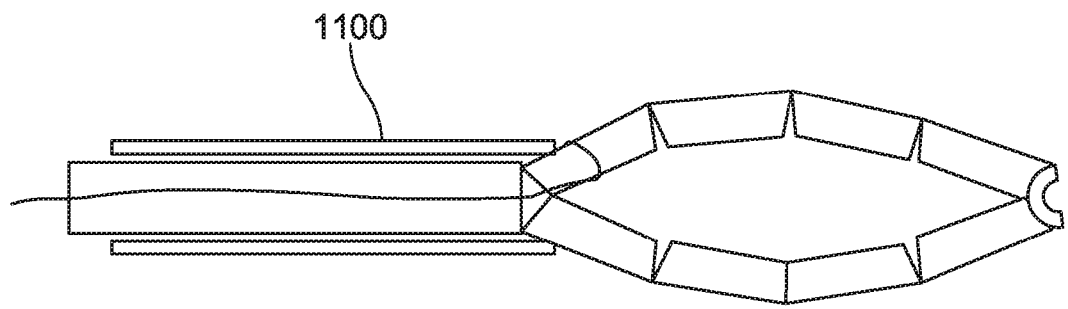
Figure 18C:
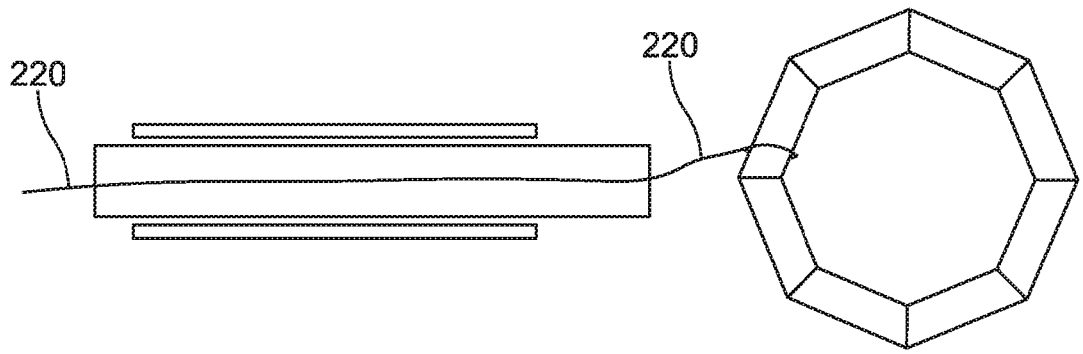
Figure 18D:
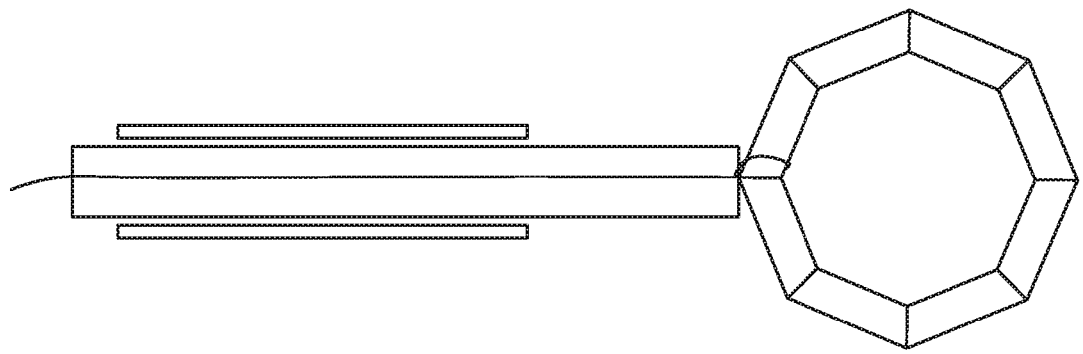
Figure 19A:
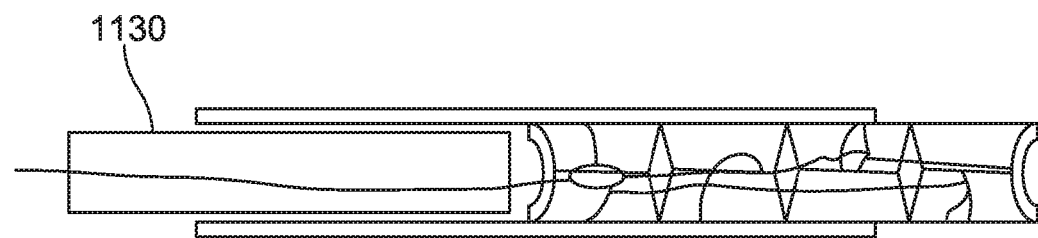
FIGS. 19A-19D depicts an embodiment of a self-opening magnetic anastomosis device that includes a guide element coupled to a plurality of radial elements coupled to magnetic segments, wherein the guide elements facilitates placement of the magnetic device in a deployment configuration.
Figure 19B:
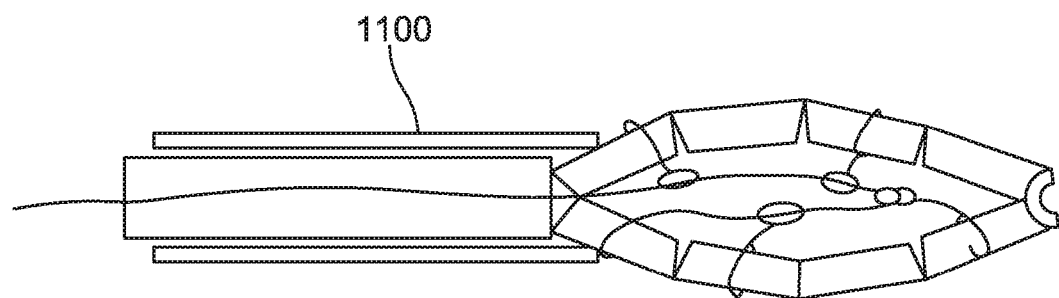
Figure 19C:
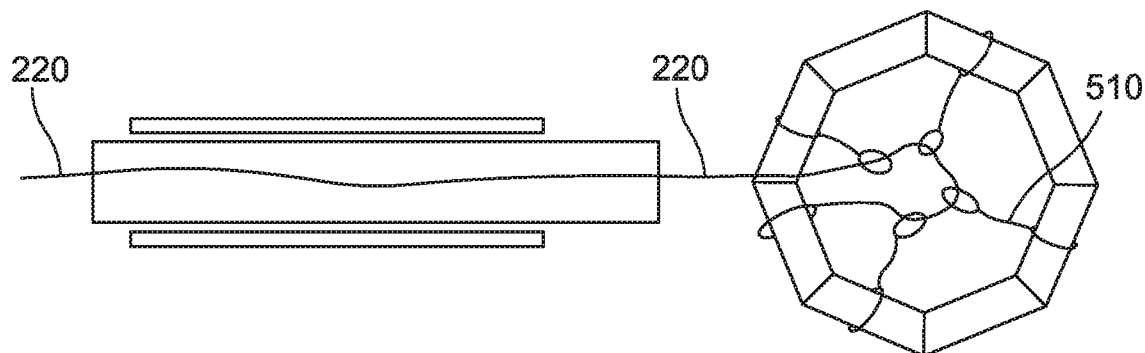
Figure 19D:
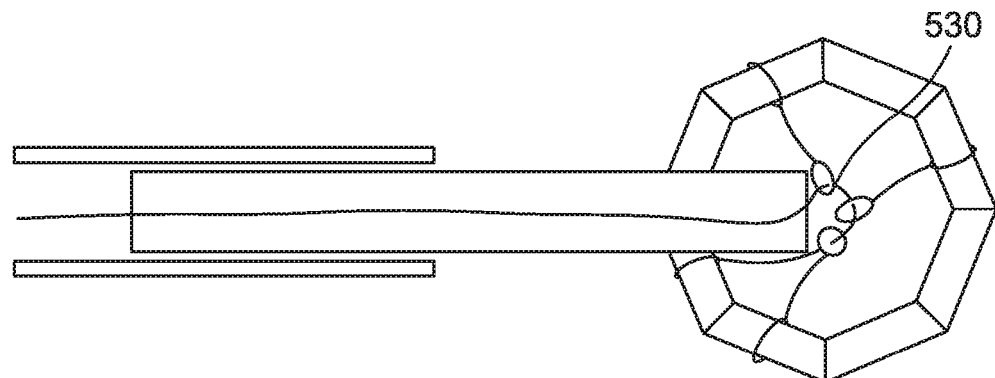
Figure 20A:
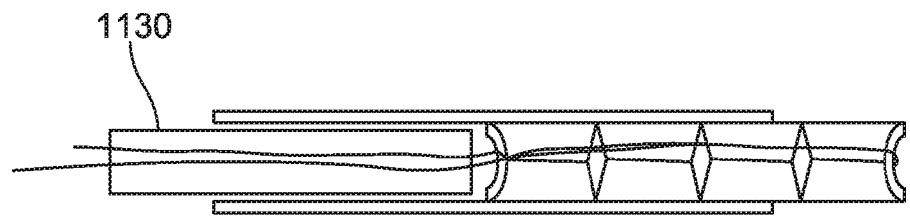
FIGS. 20A-20D depict an embodiment of a self-opening magnetic anastomosis device that includes two guide elements coupled to the connection members, wherein the guide element facilitates closure of the device and placement of the magnetic device once in a deployment configuration.
Figure 20B:
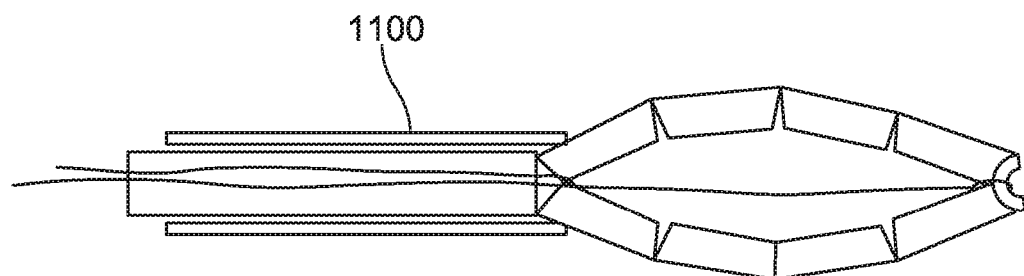
Figure 20C:
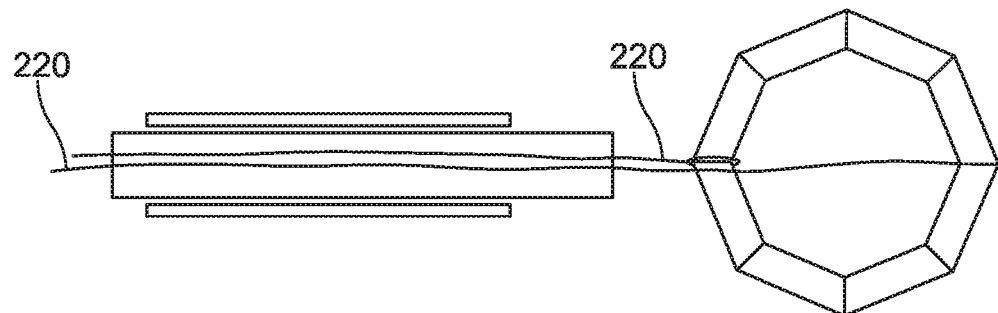
Figure 20D:
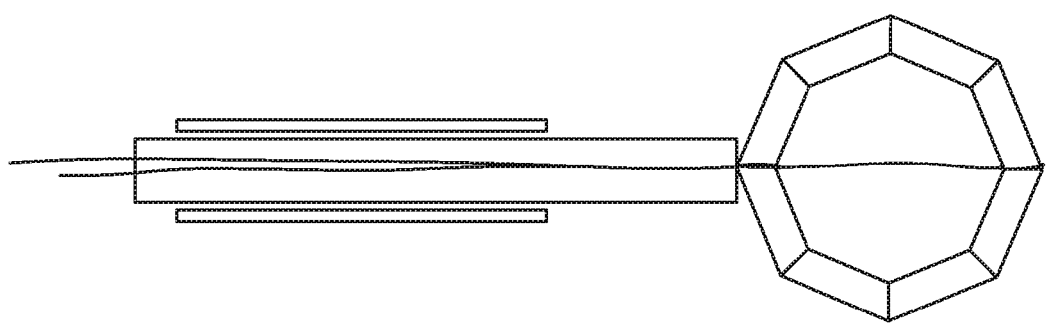
Figure 21A:
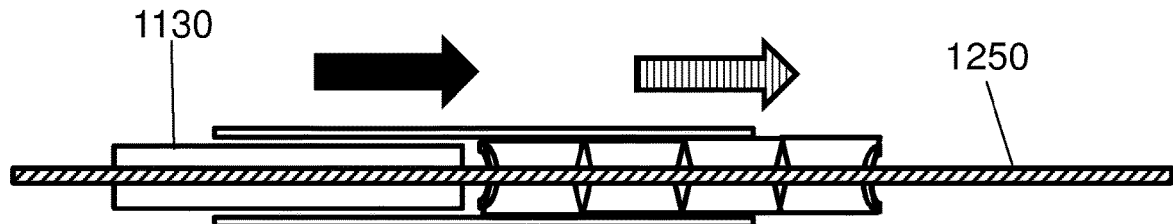
FIGS. 21A-21D depict deployment of a self-opening magnetic device using a guidewire. The self-opening device is advanced over the guidewire with a pusher while the device is kept in a delivery configuration by a sheath. Once the device is in place, the sheath can retracted allowing the device to assume a deployment configuration. The embodiment shown in FIGS. 21A-21D may additionally include one or more guide element(s) (not shown) to facilitate closure of the device and placement after transforming into a deployment configuration.
Figure 21B:
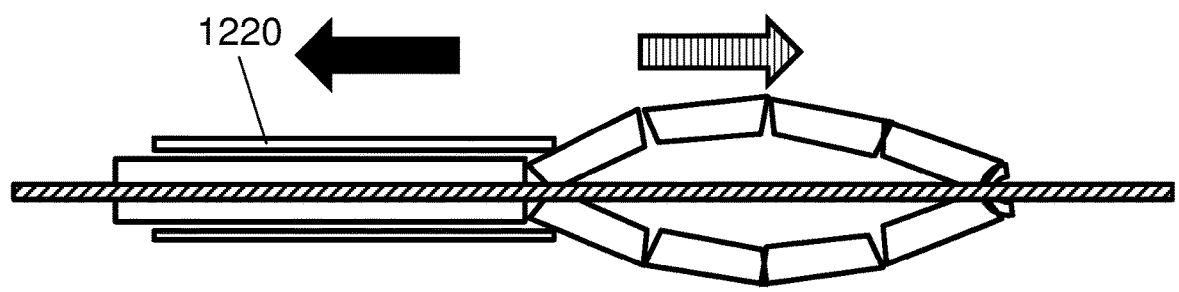
Figure 21C:
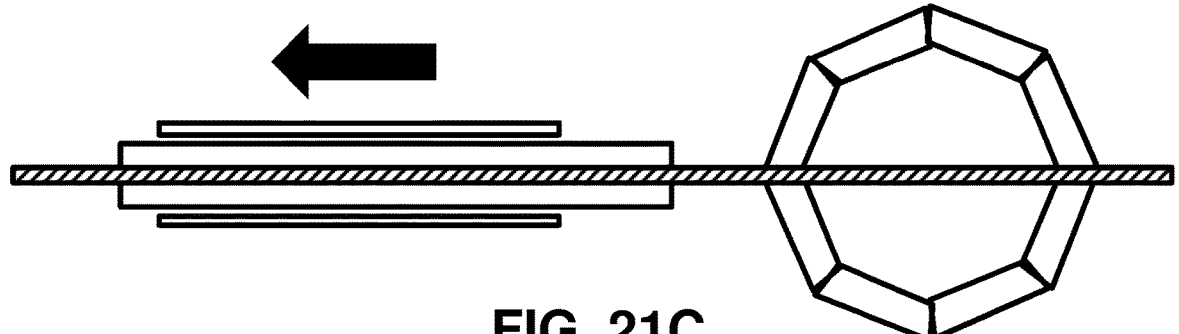
Figure 21D:
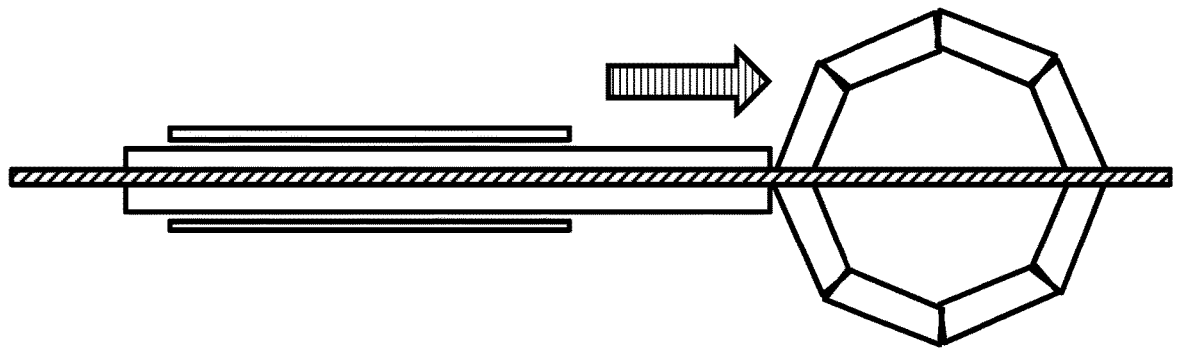
Figure 22:
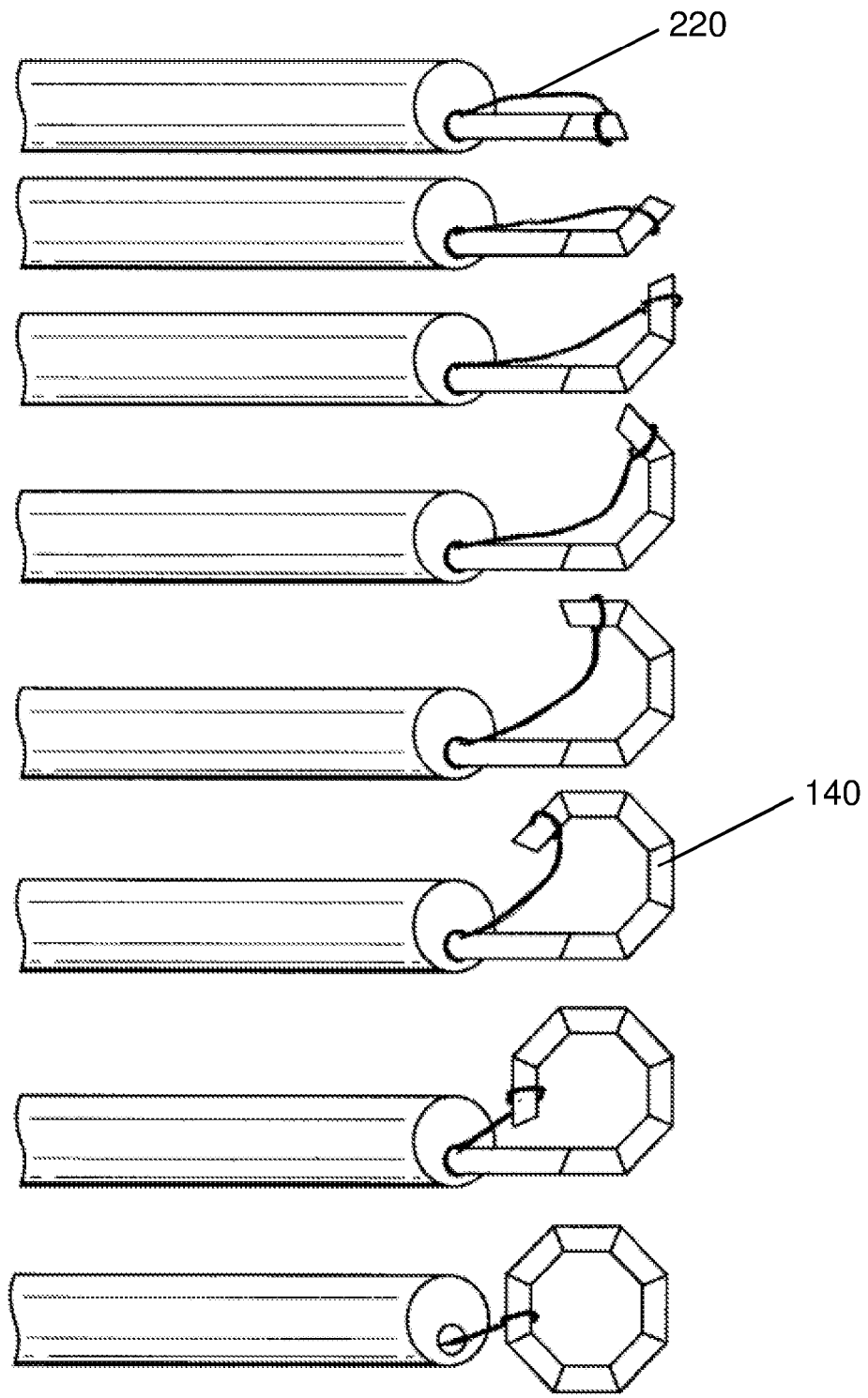
FIG. 22 depicts an embodiment of a self-closing magnetic anastomosis device that includes a guide element coupled to an magnetic segment. The guide element facilitates placement of the magnetic device in a deployment configuration.

Additionally, like the self-opening devices of FIGS. 9A-10B, the self-closing devices of FIGS. 12-15 can have a variety of magnetic polar arrangements, giving a user the ability to tune the amount of attractive force between devices at a distance. Typically, the arrangement of the magnetic segments is preset prior to attachment of the polygon-closing assembly 120, as shown in FIGS. 12-15. Because the polygon-closing assembly is non-magnetic, the completed self-closing device will have segments with polarities dictated by the polarities of the underlying magnetic segments 140, as shown in FIGS. 13-15. Again, the octagonal structures of FIGS. 12-15 are illustrative, and should not be seen as limiting. In other words, self-closing structures that create squares, hexagons, decagons, dodecagons, tetradecagons, hexadecagons, octodecagons, or icosagons can be formed in a similar manner. Additionally, self-closing magnets may be constructed from an odd number of magnetic segments, including magnetic bipoles, as shown in the drawings, or magnetic quadrupoles, hexapoles, or octapoles, as may be required. It is not necessary that each magnetic segment is the same size or length.

Accordingly, the self-closing devices, constructed from linked magnetic multipole segments 140, will form a polygon when extruded from the end of a delivery lumen, e.g., through a trocar or a working channel of an endoscope 200, as shown in FIG. 16. As each successive magnetic segment 140 emerges from the end of the working channel 200 into the surgical field, the polygon-closing assembly 120 constrains the segment against out-of-polygonal plane deflection and the segments' mutual attractions close each miter joint 260 in the correct inward direction, sequentially correct and, as the last segment is extruded, to close the polygonal magnetic ring. Furthermore, when the devices are constructed with symmetric miter joints and have their magnetic poles aligned with the annular axis of the polygon, the total magnetic force normal to the mating surfaces is maximized. The magnetic forces increase the mechanical stability of a set of coupled magnets while speeding anastomosis formation due to the intense compressive force on the trapped tissues.

In many instances, it is beneficial to be able to manipulate the location of a device after it has been delivered to a tissue. While the device can be manipulated with conventional tools such as forceps, it is often simpler to manipulate the location of the deployed device with a guide element 220, such as a suture or wire. As shown in FIGS. 17, 18A-18D, 19A-19D, 20A-20D, 21A-21D, and 22, a variety of attachment points can be used to provide control over the location and deployment of a self-opening or a self-closing magnetic anastomosis device. The guide element 220 may extend proximally away from the surgical field and emerge, e.g., from a port or from the proximal end of the working channel of an endoscope.

For example, as shown in FIGS. 18A-18D and 22, the guide element 220 may be coupled to a single distal segment such that, upon deployment, the single distal segment results in an attachment point that provides translational freedom of movement. It is also notable that in the self-closing configuration shown in FIG. 22, the guide element 220 allows a closing force to be applied to the distal-most segment. That is, in the event that one or more segments should become entangled with tissue, or otherwise prevented from closing, a proximal pulling force with the guide element 220 can help the device to complete self-assembly. Furthermore, once the device has achieved its deployed configuration, the device can be positioned with the guide element 220 to be mated with another device (not shown in FIGS. 18A-18D and 22) as described above. While it is not shown in FIG. 22, it is envisioned that additional structures, such as a pusher 1130, shown in FIGS. 18A-18D and 19A-19D may be used to deploy the device at the desired location. The pusher will typically be formed from a rigid non-interactive material, such as Teflon™ or other polymer approved for surgical applications.

The guide element 220 can be fabricated from a variety of materials to achieve the desired mechanical properties and bio-compatibility. The guide element 220 may be constructed from metal, e.g., wire, e.g., stainless steel wire, or nickel alloy wire. The guide element may be constructed from natural fibers, such as cotton or an animal product. The guide element may be constructed from polymers, such as biodegradable polymers, such as polymers including repeating lactic acid, lactone, or glycolic acid units, such as polylactic acid (PLA). The guide element may also be constructed from high-tensile strength polymers, such as Tyvek™ (high-density polyethylene fibers) or Kevlar™ (para-aramid fibers). In an embodiment, guide element 220 is constructed from biodegradable suture, such as VICRYL™ (polyglactin 910) suture available from Ethicon Corp., Somerville, N.J.

The guide element 220 can be coupled to the self-closing or self-opening device with a number of different configurations and attachment mechanisms. Additionally, the guide elements can be used in the same configurations regardless of the magnetic polar configuration of the devices. The guide element may be simply tied to the device, or the guide element 220 can be attached to the device with an adhesive, e.g., acrylate glue, or with a fastener, such as a clip, screw, or rivet.

Figure 23:
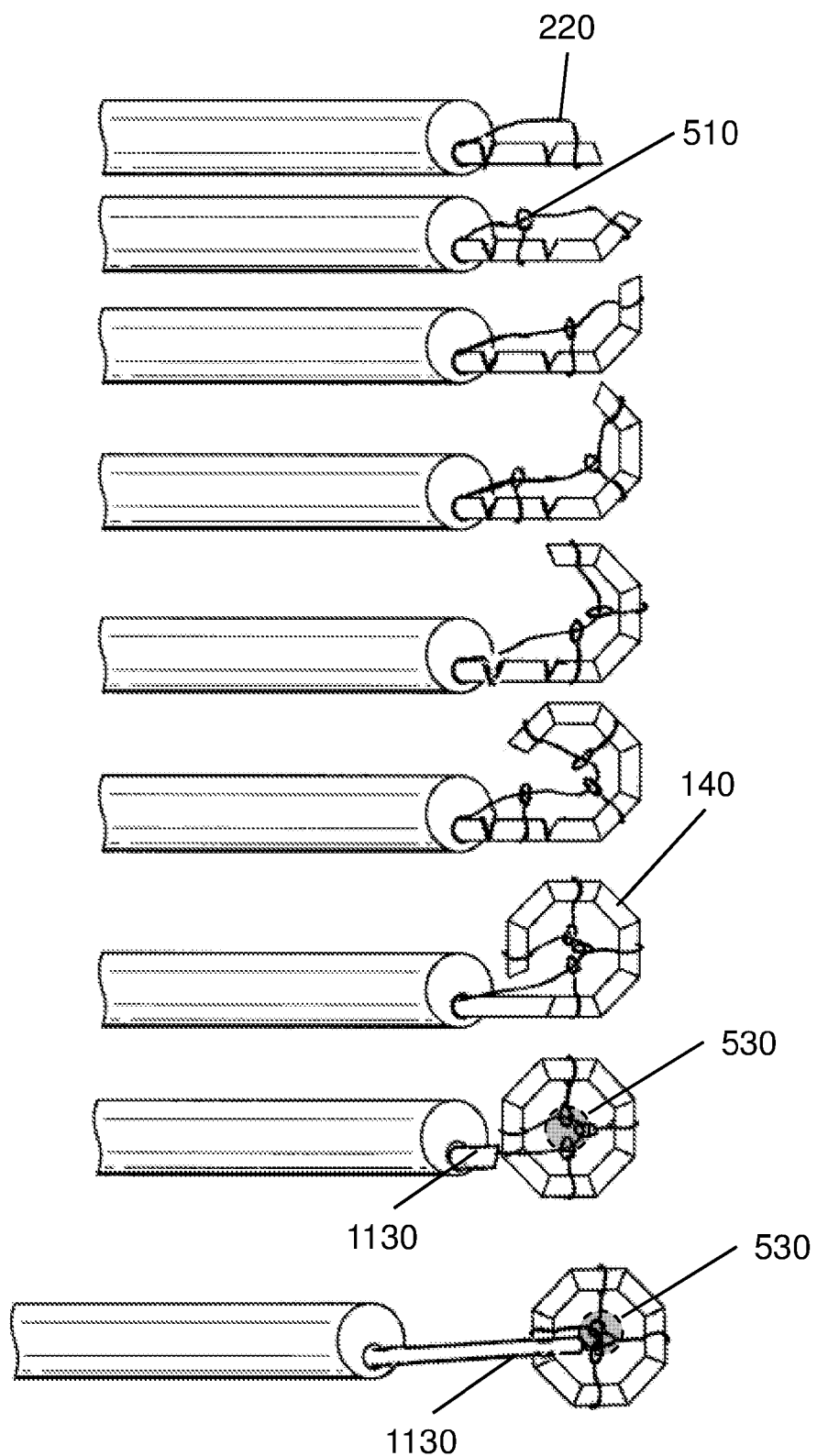
FIG. 23 depicts an embodiment of a self-closing magnetic anastomosis device that a guide element coupled to a plurality of radial elements coupled to magnetic segments. The guide elements facilitates placement of the magnetic device in a deployment configuration.

In other embodiments, such as shown in FIGS. 19A-19D and 23, the guide element 220 may be attached to, or configured to interact with, more than one part of the device. For example, FIGS. 19A-19D show a self-opening device, wherein a guide element 220 is coupled to the distal-most segment of a self-opening device, and configured to interact with radial members 510 that facilitate assembly and placement of the device. Alternatively, as shown in FIGS. 20A-20D, two guide elements 220 may be coupled to the hinges to facilitate conversion from a delivery configuration to a deployed configuration. It should be noted that the guide elements 220 shown in FIGS. 20A-20D would be on top of each other and taught when pulled, but have been shown apart for ease of viewing. Additionally in FIGS. 20A-20D, the pusher 1130 can be used to manipulate the device once it has achieved a deployed configuration. Also, as shown in FIG. 23, a guide element 220 may be coupled to the distal-most segment of a self-closing device, and configured to interact with radial members 510 that facilitate assembly and placement of the device. Furthermore, as shown in FIG. 23, proximal force on the guide element 220 helps the device to close. As shown in FIGS. 19A-19D and 23, the radial members 510 also establish a center 530 of the device, which is coupled to the guide element 220 when the device has achieved a deployment configuration and the guide element 220 is pulled taut. The center 530 of the device can then be delivered to a desired location, e.g., opposite a mating device on the other side of a tissue.

FIGS. 21A-21D show a different delivery technique, in which a guidewire 1250 is delivered to the area where an anastomosis is to be formed, after which a self-opening device can be delivered to the location using a pusher 1130 (motion shown with hashed arrow) while a sheath 1220 (motion shown with black arrow) is used to keep the self-opening device in a delivery configuration. Once the device has been delivered to the area, the sheath 1220 can be removed proximally, thereby allowing the self-opening device to transform to a deployment configuration. Once the sheath 1220 has been retracted suitably, the pusher 1130 can be used to place the device or help it to mate with a joining device. The delivery and deployment may be visualized, e.g., with fluoroscopy or ultrasound, and the device and the pusher 1130 may include markers, such as radiopaque markers, to facilitate visualization. Additionally, while not shown in FIGS. 21A-21D, the device may include one or more guide elements 220 to improve deployment or to facilitate placement.

Like the guide elements 220, the radial members 510 can be fabricated from a variety of materials to achieve the desired mechanical properties and bio-compatibility. The radial members 510 may be constructed from metal, e.g., wire, e.g., stainless steel wire, or nickel alloy wire. The guide element may be constructed from natural fibers, such as cotton or an animal product. The guide element may be constructed from polymers, such as biodegradable polymers, such as polymers including repeating lactic acid, lactone, or glycolic acid units, such as polylactic acid (PLA). The guide element may also be constructed from high-tensile strength polymers, such as Tyvek™ (high-density polyethylene fibers) or Kevlar™ (para-aramid fibers). In an embodiment, the radial members 510 are constructed from biodegradable suture, such as VICRYL™ (polyglactin 910) suture available from Ethicon Corp., Somerville, N.J. Additionally, the radial members 510 can be used in the same configurations regardless of the magnetic polar configuration of the devices.

EXAMPLES

Example 1: Calculation of Azimuthal Potentials

Azimuthal patterns were calculated for each of the self-opening configurations shown in FIGS. 24-29.

The calculations begin with the assumption of perfect repulsive symmetry across the centerline of the self-opening rings, the line between the two internal hinges at either end of the delivery configuration and its two parallel rows of four magnet segments. With this assumed symmetry we need only enumerate the possible combinations of N's and S's along one of the four-segment 'sides.' There are only 16 such arrangements, $2^4$, which can be easily spelled out:

1) NNNN
2) NNNS
3) NNSN
4) NSNN
5) SNNN
6) NNSS
7) NSSN
8) SSNN
9) SNNS
10) SNSN
11) NSNS
12) NSSS
13) SNSS
14) SSNS
15) SSSN
16) SSSS

Because of centerline mirror symmetry, it can't matter from which end we start with the calculation. A pattern left-to-right must be the same entity as the same pattern from right-to-left, as well as being the same as the 'reverse pattern (N/S swap equivalent to a ring flip)' in either direction. So 1=16, 2=15=5=12, 3=14=4=13, 6=8, 7=9, 10=11 and there are only 6 distinct patterns: 1,2,3,6,7,10

Figure 9A:
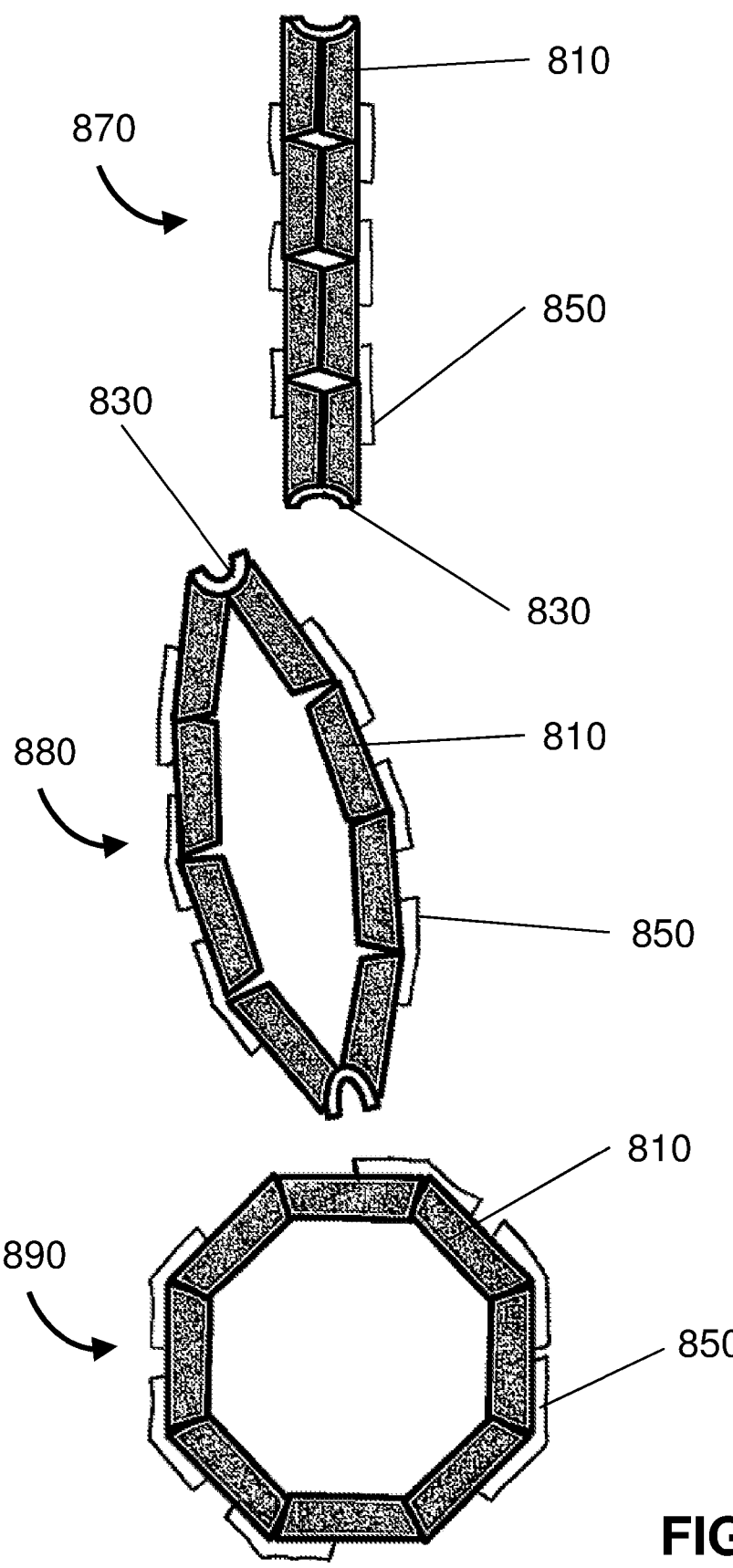
FIG. 9A is a close-up view of a self-opening magnetic anastomosis device of the invention including connection members, such as hinges, at the ends and polygon-opening members between adjacent magnetic segments. In the embodiment of FIG. 9A, all of the poles of the magnetic segments are arranged in the same direction.
Figure 9B:
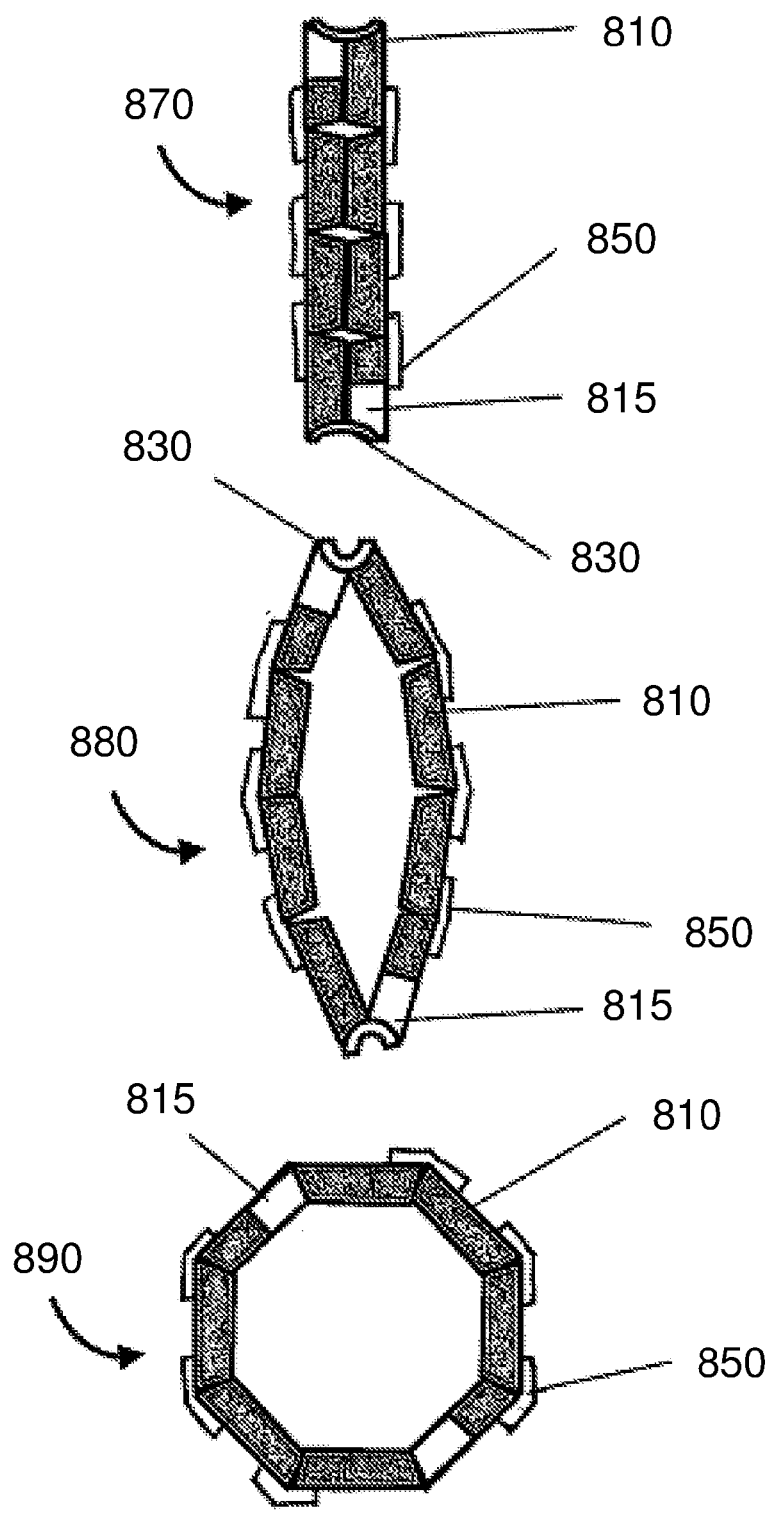
FIG. 9B is a close-up view of a self-opening magnetic anastomosis device of the invention including connection members at the ends and polygon-opening members between adjacent magnetic segments. In the embodiment of FIG. 9B, two of the bipolar magnets of FIG. 8 have been replaced with quadrupolar segments, which facilitate closure of the connection members.
Figure 9C:
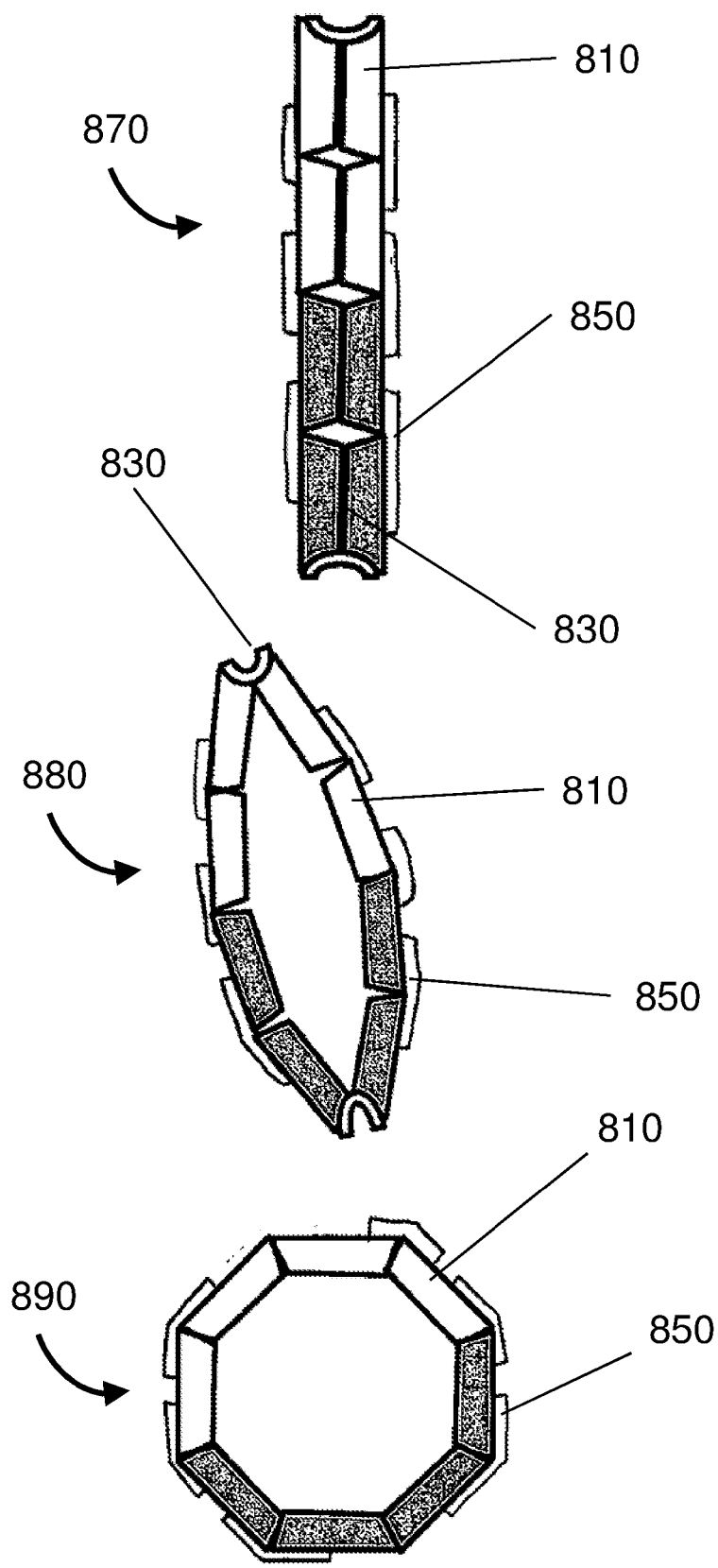
FIG. 9C is a close-up view of a self-opening magnetic anastomosis device of the invention including connection members at the ends and polygon-opening members between adjacent magnetic segments. In the embodiment of FIG. 9C, half of the poles of the magnetic segments are arranged toward the top of the polygon and half of the poles of the magnetic segments are arranged toward the bottom of the polygon.
Figure 9D:
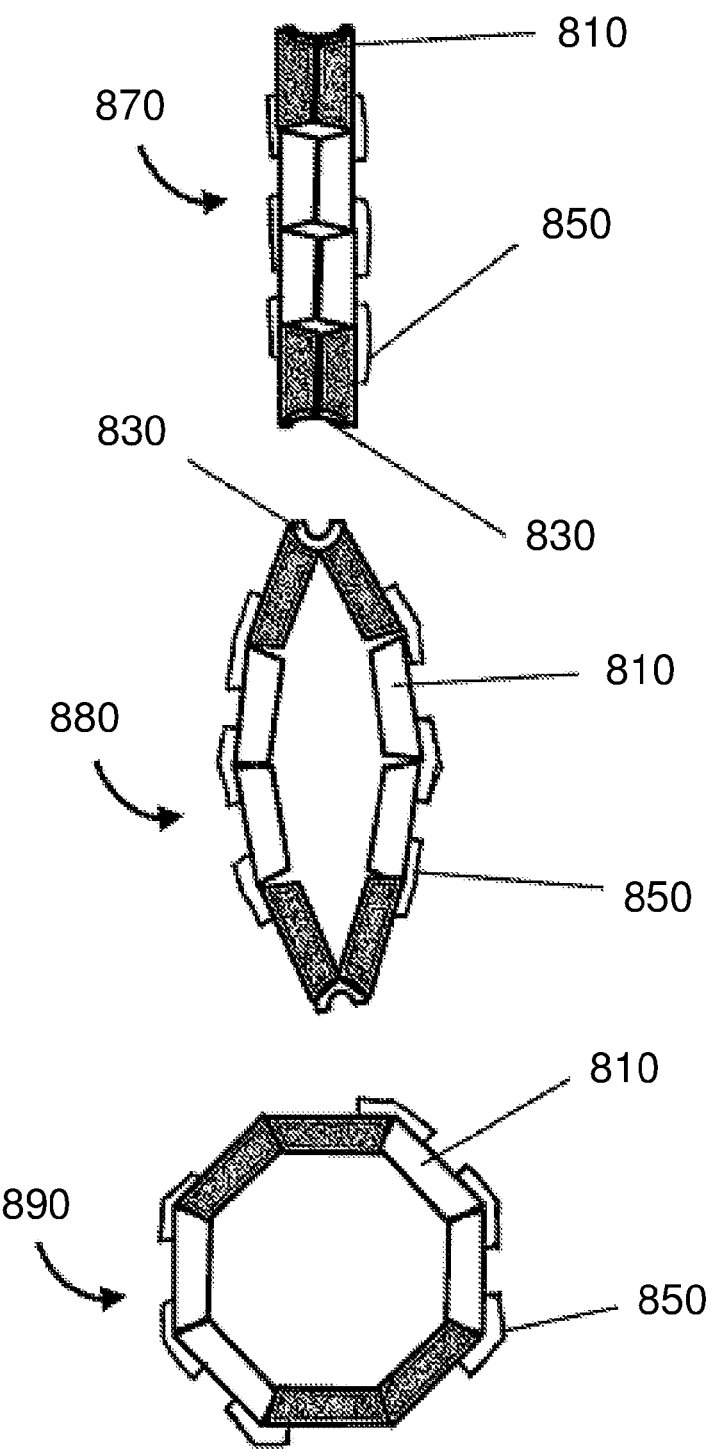
FIG. 9D is a close-up view of a self-opening magnetic anastomosis device of the invention including connection members at the ends and polygon-opening members between adjacent magnetic segments. In the embodiment of FIG. 9D, the north poles of the magnetic elements coupled to the connection members are arranged toward the top of the polygon, and the middle elements have their poles directed to the bottom of the polygon.
Figure 24:
FIG. 24 depicts calculations of potential wells in an octagonal self-opening device having an NNNN alignment.
Figure 24:
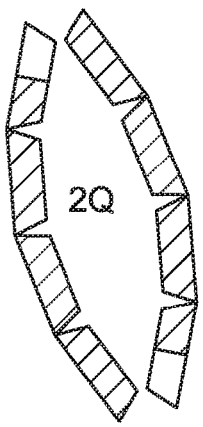
Figure 24:
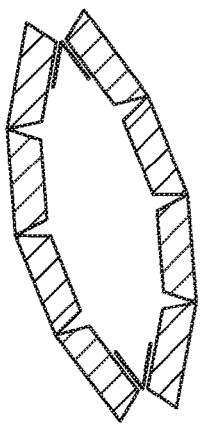
Figure 24:
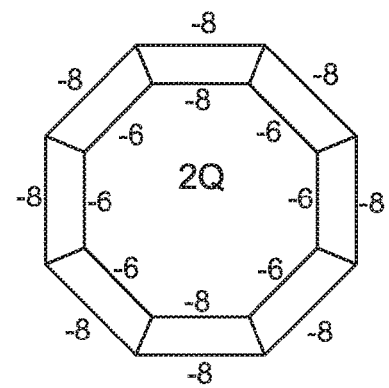
Figure 24:
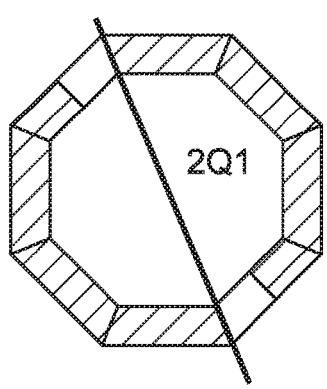
Figure 24:
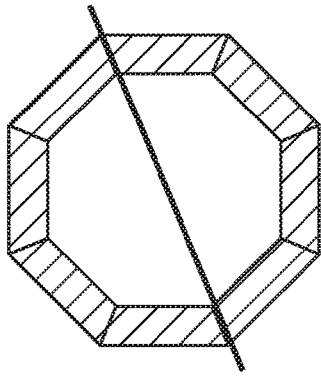
Figure 24:
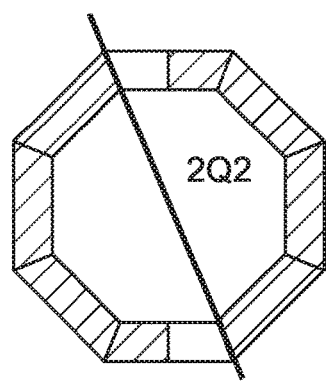
Figure 25:
FIG. 25 depicts calculations of potential wells in an octagonal self-opening device having an NNNS alignment.
Figure 25:
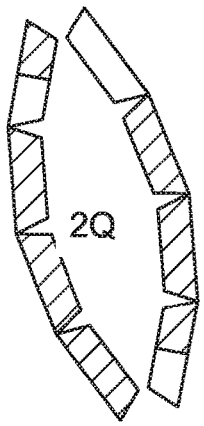
Figure 25:
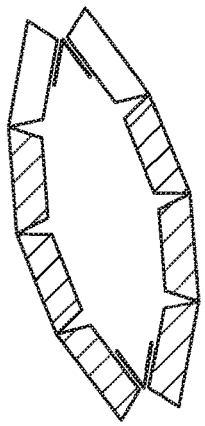
Figure 25:
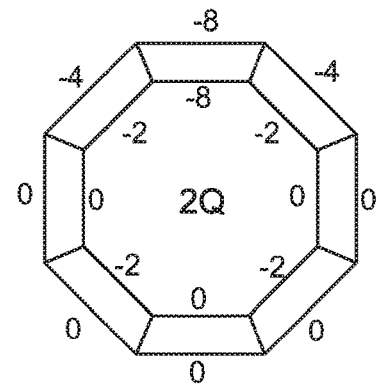
Figure 25:
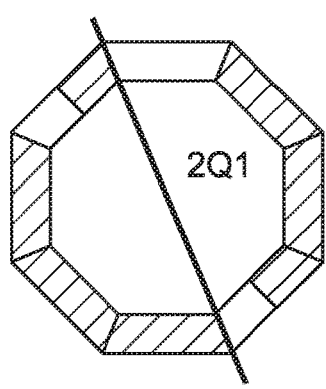
Figure 25:
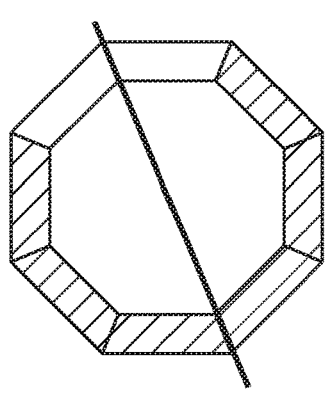
Figure 25:
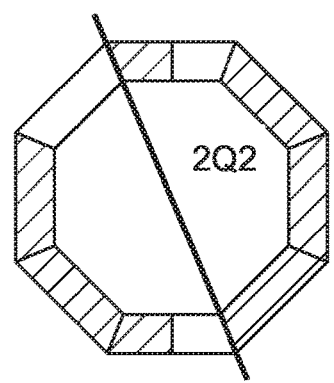
Figure 26:
FIG. 26 depicts calculations of potential wells in an octagonal self-opening device having an NNSN alignment.
Figure 26:
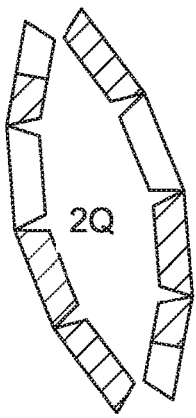
Figure 26:
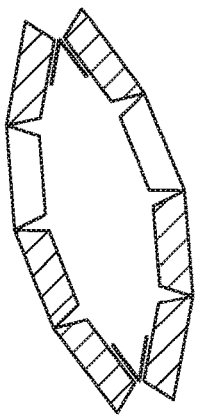
Figure 26:
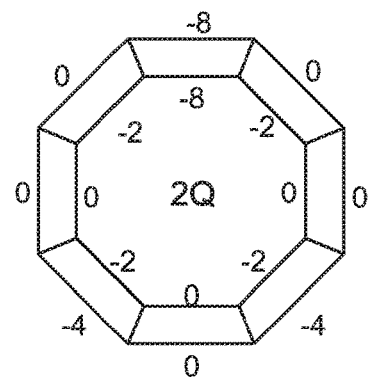
Figure 26:
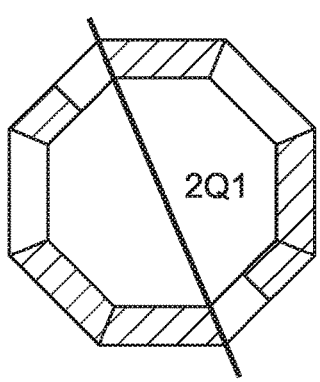
Figure 26:
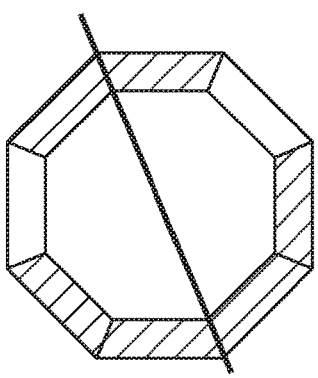
Figure 26:
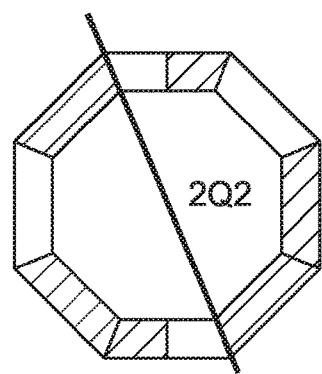
Figure 27:
FIG. 27 depicts calculations of potential wells in an octagonal self-opening device having an NNSS alignment.
Figure 27:
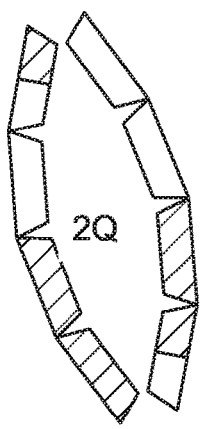
Figure 27:
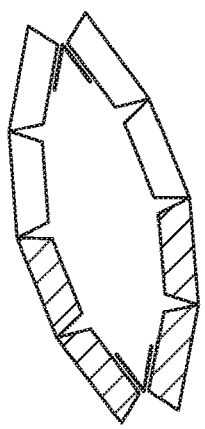
Figure 27:
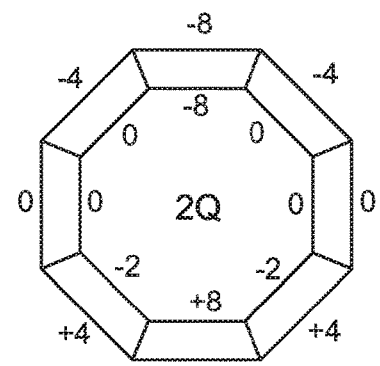
Figure 27:
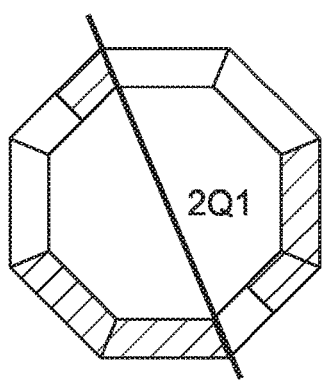
Figure 27:
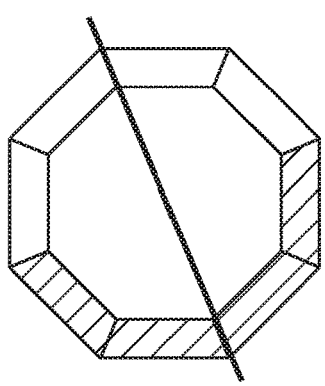
Figure 27:
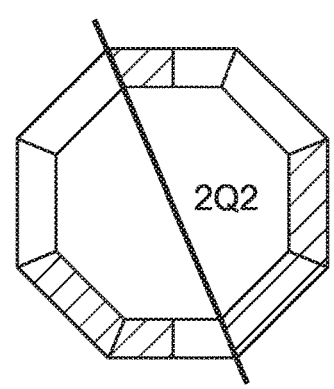
Figure 28:
FIG. 28 depicts calculations of potential wells in an octagonal self-opening device having an NSSN alignment.
Figure 28:
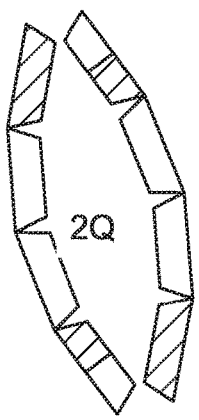
Figure 28:
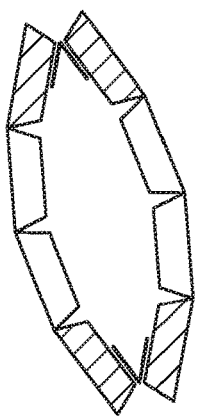
Figure 28:
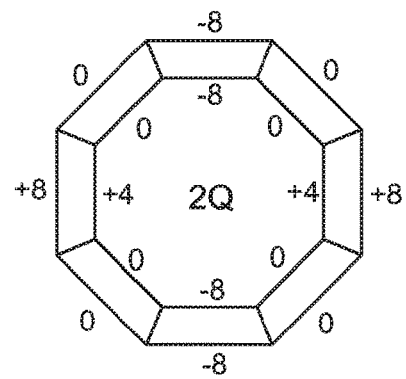
Figure 28:
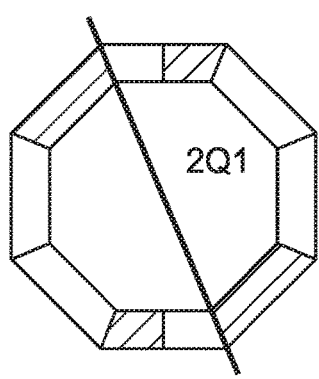
Figure 28:
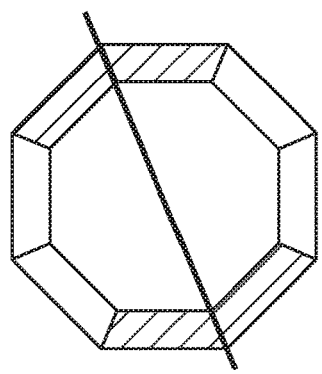
Figure 28:
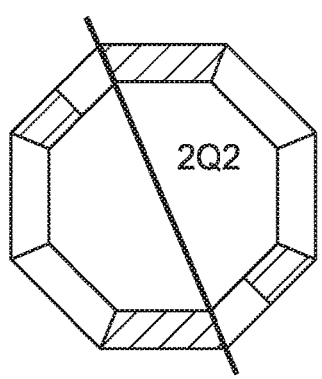
Figure 29:
FIG. 29 depicts calculations of potential wells in an octagonal self-opening device having an NSNS alignment.
Figure 29:
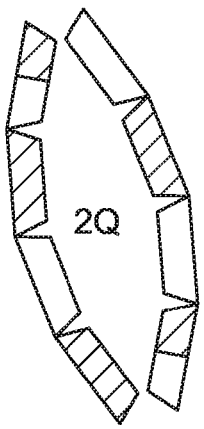
Figure 29:
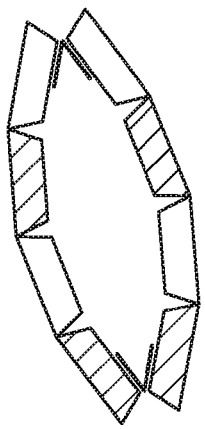
Figure 29:
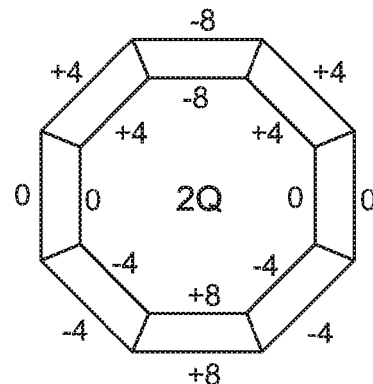
Figure 29:
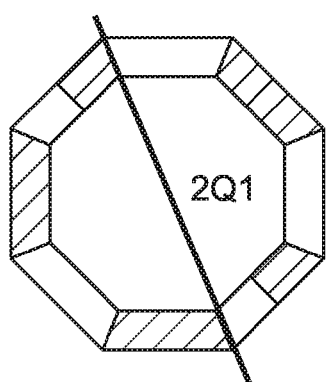
Figure 29:
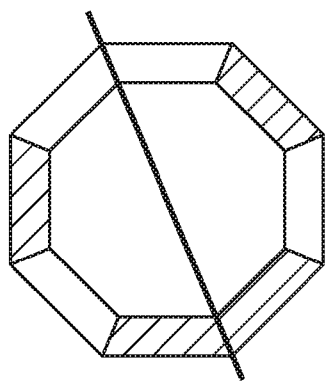
Figure 29:
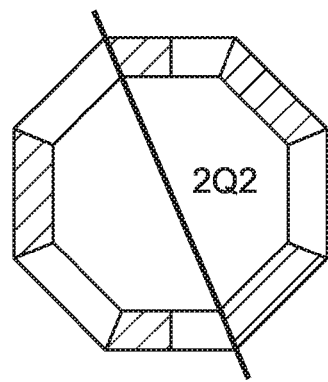

Configuration 1=16)=FIGS. 9A, 9B, and 24.
Configuration 2=5)=12)=15)=FIG. 25.
Configuration 3=4)=13)=14)=FIG. 26.
Configuration 6=8)=FIGS. 9C and 27.
Configuration 7=9)=FIGS. 9D and 28.
Configuration 10=11)=FIGS. 10A and 29.

The azimuthal properties of each pattern were calculated by drawing each octagonal magnet pattern onto duplicate mylar sheets. The potential energy of each segment's interaction with its mating neighbor is either −1, +1 or 0, attractive-repulsive-neutral. [As an approximation, each of the two inserted quadrupolar segments are deemed to have no interaction with any dipole segment; however a full interaction when one quadrupolar segment aligns with other quadrupole.] After the initial calculation, one of the mylar sheets is rotated 45 degrees and the new potential energy tabulated. Repeating this rotation and calculation step eight times results in a list of 8 numbers that describe the rings' interaction through one complete in-plane revolution relative to the other. Additional details of the calculations are presented below.

The numbers from the calculation are tabulated in an octagonal array (i.e., 12, 1:30, 3, 4:30, 6, 7:30, 9, 10:30 on a clockface) where an adjacent number represents the potential energy of the rings after 45 degree rotation of one of the rings. The potential energy of the ring-pair is actually a smooth curve connecting these most easily calculated locations. Using this presentation, we can tabulate the azimuthal behavior of the six distinct patterns shown in FIGS. 24-29 (2Q versions thereof) as well as the potential energy of a closed ring (on the right), the sum of the miter interactions (compared with −8 of the earlier, completely self-assembling rings).

| | | |
|---|---|---|
| (1) −8 −8 −8 −8 −8 −8 −8 −8 | 8 repel (R) | +8 |
| (2) −8 −2 0 −2 0 −2 0 −2 | 4 attract (A)/4 repel (R) | 0 |
| (3) −8 +2 0 −2 0 −2 0 +2 | 6A2R | −4 |
| (6) −8 0 0 0 +8 0 0 0 | 4A4R | 0 |
| (7) −8 0 +4 0 −8 0 +4 0 | 6A2R | −4 |
| (10) −8 +4 0 −4 +8 −4 0 +4 | 8R | +8 |

Upon making the calculations, the following trends are noted:

Configuration 1 (FIG. 24) is unique in the absence of variation of attractive force with rotation. While there is no azimuthal variation, the lack of rotational force could potentially lead to mismatched devices and deviation in size and shape of the anastomosis. However, with proper placement, it is unlikely that the lack of rotational wells will be problematic. It is noteworthy that all of the mitered joints are repulsive in Configuration 1 (or almost all, if quadrupole segments are used at the end). For this reason, it may be beneficial to deploy self-opening devices of configuration 1 using guide elements, e.g., as discussed above.

Configuration 2 (FIG. 25) Numerous attractive wells, only one full depth.

Configuration 3 (FIG. 26) Numerous attractive wells, only one full depth, surrounded by 25% repulsive barriers.

Configuration 6 (FIG. 27) Good potential. While Configuration 6 has rotational potential wells, the wells are well-defined and aid alignment of the devices. Additionally, the force at a distance is almost as strong as Configuration 1. See, e.g., FIG. 7.

Configuration 7 (FIG. 28) Good potential. Slightly less force at a distance, rotational wells facilitate alignment, but provide more maneuverability because there are two equal wells with 180° of rotation of one device.

Configuration 10 (FIG. 29) Numerous potential wells, only one full depth, flanked by 50% repulsive barriers; the multiple rotational wells may make alignment more difficult.

Calculation of the repulsive and attractive forces for each self-opening configuration, with and without quadrupole end segments, is calculated as detailed, below. Each configuration, i.e., as shown in FIGS. 24-29, has multiple diagrams, noted i, ii, iii, . . . viii. (Cross-hatched is N, solid is S.) Diagrams i, ii, and iii depict the configuration without quadrupolar segments, i.e., "nonQ" versions, whereas iv, v, and viii represent the configuration with the addition of one quadrupolar magnetic segment at each end, i.e., the "2Q" versions.

Because there is repulsion across each inner hinge, there is some advantage of adding an additional reversal, a quadrupole segment, that allows for attraction across what is otherwise repulsive miter. (No short range loss of force; some loss on long range interaction.) This 2Q version, with one for each inner hinge, is depicted in diagrams iv, v, and viii. (There are actually two ways to introduce the Q's, mirror images across the centerline. They are non-superimposable mirror images with equivalent behavior.)

Separately, each configuration includes a diagram vi that is a depiction of the ring's rotational interaction (nonQ numbers outside, 2Q numbers inside). With both rings perfectly aligned there is a maximal 8 units of attraction between all mated segments, depicted as −8 implying a potential energy well. As one magnet is held fixed and the other is rotated to one of the other 7 aligned positions the new potential energy of the ring couple is displayed there accordingly. +8 represents a condition of complete repulsion between all 8 pairs and 0 a balance between 4 attractive and 4 repulsive segment pairs. −2 slight attraction. +2 slight repulsion. The lower the number the greater the rings' total attractive force in that orientation. Additionally, there is an applied torque proportional to the change in energy as function of azimuthal angle. Configuration 1, diagram vi shows that coupling of these 'unipolar rings' would not require rotation, nor could coupling induce rotation. Configuration 2, diagram vi shows that the 2Q (inner) version would have distracting weak minima at 4:30 and 7:30 from the real direction. Configuration 3, diagram vi shows strong 'half-deep' wells in the nonQ configuration may make alignment tricky during a procedure. Configuration 6, diagram vi suggests beneficial properties both in terms of alignment and closing, and has favorable long-distance properties, as discussed above. Configuration 7, diagram vi suggests that configuration 7 doesn't have to rotate as far as configuration 6, but has slightly inferior long distance interactions. Configuration 10, diagram vi, suggests a variety of local minima, which may result in disfavored performance. Configuration 10 additionally experiences less attractive force at a distance, which may make coupling more difficult through, e.g., thick tissues.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A self-opening magnetic compression anastomosis device comprising:
an assembly comprising:
a first cluster comprising a plurality of magnetic segments coupled end-to-end, and
a second cluster comprising a plurality magnetic segments coupled end-to-end,
a first connection member connected to a magnetic segment of the first cluster and a magnetic segment of the second cluster;
a second connection member connected to a magnetic segment of the first cluster and a magnetic segment of the second cluster;
a first polygon-opening member coupled to at least two magnetic segments of the first cluster; and
a second polygon-opening member coupled to at least two magnetic segments of the second cluster,
wherein the assembly comprises:
a delivery configuration wherein the magnetic segments of the first cluster form a first row and the magnetic segments of the second cluster form a second row and wherein each of the first connection member and the second connection member joins an end of the first row to an end of the second row, and
a deployed configuration wherein the magnetic segments are coupled end-to-end to form a polygon comprising a plane and having an out-of-plane axis.

2. The magnetic compression device of claim 1, wherein:
the magnetic segments connected to the first connection member have north poles aligned relative to one another with respect to the out-of-plane axis when the assembly is in the deployed configuration, and
the magnetic segments connected to the second connection member have north poles aligned relative to one another with respect to the out-of-plane axis when the assembly is in the deployed configuration.

3. The magnetic compression device of claim 2, wherein the north poles of the magnetic segments connected to the first connection member are aligned with the north poles of the magnetic segments connected to the second connection member.

4. The magnetic compression device of claim 2, wherein the north poles of the magnetic segments connected to the first connection member are anti-aligned with the north poles of the magnetic segments connected to the second connection member.

5. The magnetic compression device of claim 1, wherein adjacent magnetic segments in the deployed configuration have north poles that alternate in orientation with respect to the top and bottom of the polygon.

6. The magnetic compression device of claim 1, wherein, when the assembly is in the deployed configuration:
the first polygon-opening member is coupled to an exterior surface of the at least two magnetic segments of the first cluster, and
the second polygon-opening member is coupled to an exterior surface of the at least two magnetic segments of the second cluster.

7. The magnetic compression device of claim 1, wherein:
the first polygon-opening member is coupled to each magnetic segment of the first cluster, and
the second polygon-opening member is coupled to each magnetic segment of the second cluster.

8. The magnetic compression device of claim 7, wherein:
the first polygon-opening member restricts movement of the magnetic segments of the first cluster relative to the plane of the polygon, and
the second polygon-opening member restricts movement of the magnetic segments of the second cluster relative to the plane of the polygon.

9. The magnetic compression device of claim 8, wherein:
the first polygon-opening member prohibits movement of the magnetic segments of the first cluster out of the plane of the polygon, and
the second polygon-opening member prohibits movement of the magnetic segments of the second cluster out of the plane of the polygon.

10. The magnetic compression device of claim 1, wherein a force exerted by the first polygon-opening member on the at least two magnetic segments coupled to the first polygon-opening member and a force exerted by the second polygon-opening member on the at least two magnetic segments coupled to the second polygon-opening member promote transition of the assembly from the delivery configuration to the deployed configuration.

11. The magnetic compression device of claim 1, wherein each of the first connection member and the second connection member comprises a hinge.

12. The magnetic compression device of claim 1, wherein the polygon is selected from the group consisting of a square, a rectangle, a hexagon, and an octagon.

13. A self-opening magnetic compression anastomosis device comprising:
an assembly comprising:
a first cluster comprising a plurality of magnetic segments coupled end-to-end, and
a second cluster comprising a plurality magnetic segments coupled end-to-end, a first connection member connected to a magnetic segment of the first cluster and a magnetic segment of the second cluster;
a second connection member connected to a magnetic segment of the first cluster and a magnetic segment of the second cluster;
a first radial member having a proximal end and a distal end, the distal end being coupled to a magnetic element in the first cluster;
a second radial member having a proximal end and a distal end, the distal end being coupled to a magnetic element in the second cluster; and
a guide element having a proximal end and a distal end, the distal end being coupled to the proximal ends of the first radial member and the second radial member, wherein the assembly comprises:
a delivery configuration wherein the magnetic segments of the first cluster form a first row and the magnetic segments of the second cluster form a second row and wherein each of the first connection member and the second connection member joins an end of the first row to an end of the second row, and
a deployed configuration wherein the magnetic segments are coupled end-to-end to form a polygon comprising a plane and having an out-of-plane axis.

14. The magnetic compression device of claim 13, wherein:
the magnetic segments connected to the first connection member have north poles aligned relative to one another with respect to the out-of-plane axis when the assembly is in the deployed configuration, and
the magnetic segments connected to the second connection member have north poles aligned relative to one another with respect to the out-of-plane axis when the assembly is in the deployed configuration.

15. The magnetic compression device of claim 14, wherein the north poles of the magnetic segments connected to the first connection member are aligned with the north poles of the magnetic segments connected to the second connection member.

16. The magnetic compression device of claim 14, wherein the north poles of the magnetic segments connected to the first connection member are anti-aligned with the north poles of the magnetic segments connected to the second connection member.

17. The magnetic compression device of claim 13, wherein adjacent magnetic segments in the deployed configuration have north poles that alternate in orientation with respect to the top and bottom of the polygon.

18. The magnetic compression device of claim 13, wherein a site of coupling of the distal end of the guide element to the proximal end of each of the radial members comprises an approximate center of the polygon when the assembly is in the deployed configuration.

19. The magnetic compression device of claim 13, wherein the device comprises a plurality of first radial members and a plurality of second radial members.

20. The magnetic compression device of claim 13, wherein each of the first connection member and the second connection member comprises a hinge.

* * * * *